(12) United States Patent
Shimizu et al.

(10) Patent No.: US 8,655,436 B2
(45) Date of Patent: Feb. 18, 2014

(54) HEART RATE METER AND HEART BEAT DETECTING METHOD

(75) Inventors: Hideki Shimizu, Saitama (JP); Tsuneharu Kasai, Saitama (JP)

(73) Assignee: Citizen Holdings Co., Ltd., Tokyo (JP)

( * ) Notice: Subject to any disclaimer, the term of this patent is extended or adjusted under 35 U.S.C. 154(b) by 1271 days.

(21) Appl. No.: 12/088,336

(22) PCT Filed: Sep. 5, 2006

(86) PCT No.: PCT/JP2006/317521
§ 371 (c)(1),
(2), (4) Date: Mar. 27, 2008

(87) PCT Pub. No.: WO2007/037100
PCT Pub. Date: Apr. 5, 2007

(65) Prior Publication Data
US 2009/0156948 A1 Jun. 18, 2009

(30) Foreign Application Priority Data
Sep. 27, 2005 (JP) ................................. 2005-280398

(51) Int. Cl.
*A61B 5/0402* (2006.01)
(52) U.S. Cl.
USPC ...................................................... 600/519
(58) Field of Classification Search
USPC .................. 600/508, 509, 519–521
See application file for complete search history.

(56) References Cited

U.S. PATENT DOCUMENTS 5,876,350 A * 3/1999 Lo et al. .......................... 600/519
2002/0035315 A1 3/2002 Ali et al.

FOREIGN PATENT DOCUMENTS

JP 59-32437 A 2/1984
(Continued)

OTHER PUBLICATIONS

Chinese Office Action dated Aug. 28, 2009, issued in corresponding Chinese Patent Application No. 2006800356024.
Yufang Wang et al.; "The Design of Portable Heart Rate Recorder"; Journal of Guangdong Institute for Nationalities, China Academic Journal Electronic Publishing House.
(Continued)

*Primary Examiner* — Scott Getzow
(74) *Attorney, Agent, or Firm* — Westerman, Hattori, Daniels & Adrian, LLP

(57) ABSTRACT

A heart rate meter includes a heart beat detecting unit for detecting a heart beat waveform of a living body and a signal processor 4 for detecting a heart beat from the heart beat waveform. The signal processor 4 includes a heart beat signal generating processor 5 for adding a predetermined frequency characteristic to the signal within a predetermined narrow band of the heart beat waveform to generate a heart beat signal, and a heart beat detecting processor 6 for detecting a heart beat from a waveform distortion that is added to the heart beat signal by the heart beat signal generating processor. The heart beat signal generating processor 5 subjects the signal within the predetermined narrow band of the heart beat waveform to a signal processing, thereby removing the noise component existing in the frequency band, other than the primary component of the heart beat waveform, and performs signal processing to add the predetermined frequency characteristic, thereby generating a heart beat signal in which the signal intensity of a frequency component is amplified. The heart beat detecting processor 6 detects the waveform distortion added to the heart beat signal by the heart beat signal generating processor. Even when there is a variation in the measuring condition and signal characteristics such as the frequencies and the crest values of the fundamental wave, higher harmonic, and noise component are changed, a heart beat is accurately detected.

17 Claims, 30 Drawing Sheets

(56) References Cited

FOREIGN PATENT DOCUMENTS

| | | |
|---|---|---|
| JP | 61-29730 B2 | 7/1986 |
| JP | 63-34730 A | 2/1988 |
| JP | 4-79250 B2 | 12/1992 |
| JP | 7-23916 A | 1/1995 |
| JP | 11-9564 A | 1/1999 |
| JP | 2003-310562 A | 11/2003 |
| JP | 2004-113380 A | 4/2004 |
| JP | 2004-528913 A | 9/2004 |
| JP | 2004-351110 A | 12/2004 |
| WO | 02-091918 A2 | 11/2002 |

OTHER PUBLICATIONS

Japanese Office Action dated Jan. 28, 2010, issued in corresponding Japanese Patent Application No. 2007-537564.
International Search Report of PCT/JP2006/317521, date of mailing Oct. 3, 2006.
Ishikawa, T.; "Exercise Physiology for Health and Physical Fitness"; Kyorin-shoin, pp. 75-78, Apr. 2000.
Notification of Transmittal of Translation of the International Preliminary Report on Patentability (Form PCT/IB/338) of International Application No. PCT/JP2006/317521 mailed Apr. 10, 2008 with Forms PCT/IB/373 and PCT/ISA/237.
Japanese Office Action dated Jul. 2, 2010, issued in corresponding Japanese Patent Application No. 2007-537564.

* cited by examiner

BAND PASS FILTER

SECOND-ORDER
DIFFERENTIAL PROPERTY

BAND PASS FILTER +
SECOND-ORDER DIFFERENTIAL PROPERTY

REGION FOR BODY
MOTION NOISE
DURING EXERCISE
+ DISTURBANCE NOISE
DURING EXERCISE

DETECTED SIGNAL

BAND PASS FILTER

BAND PASS FILTER
PASSING SIGNAL

SECOND-ORDER
DIFFERENTIATION

SIGNAL AFTER
SECOND-ORDER
DIFFERENTIAL
PROCESSING

DETECTED SIGNAL

BAND PASS FILTER

DETECTED SIGNAL

SECOND-ORDER
DIFFERENTIATION

DETECTED SIGNAL

NON-EXERCISE
BEFORE PROCESSING

Data 1024 (5279 - 6302) Smooth 0
Unfiltered

NON-EXERCISE
AFTER PROCESSING

Data 1024 (5279 – 6302) Smooth 0
Unfiltered

IMMEDIATELY AFTER EXERCISE INITIATION
BEFORE PROCESSING

Data 1024 (9446 – 10469) Smooth 0
Unfiltered

IMMEDIATELY AFTER EXERCISE INITIATION
AFTER PROCESSING

Data 1024 (22504 – 23527) Smooth 0
Unfiltered

DURING EXERCISE
BEFORE PROCESSING

Data 1024 (22504 - 23527) Smooth 0
Unfiltered

DURING EXERCISE
AFTER PROCESSING

Data 1024 (22504 - 23527) Smooth 0
Unfiltered

BAND PASS FILTER

SECOND-ORDER DIFFERENTIAL PROPERTY

FIRST DIFFERENTIATION

SECOND DIFFERENTIATION

THIRD DIFFERENTIATION

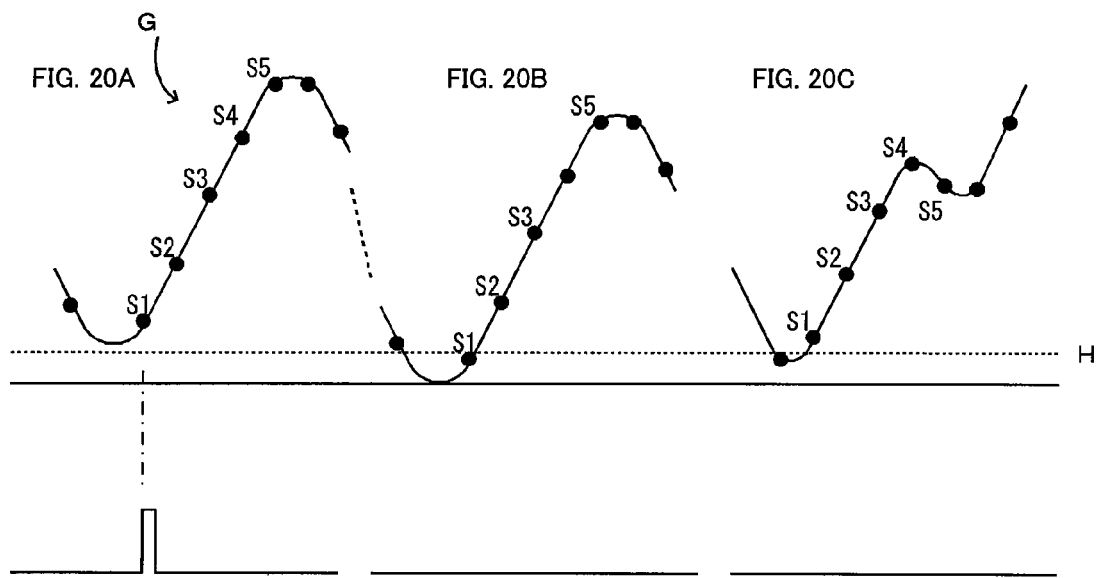

DISTURBANCE NOISE

4/1024  TIME (sec) →

BODY MOTION NOISE

4/1024                    shi2

NON-EXERCISE

Data 1024 (5279 - 6302) Smooth 0
Unfiltered

INITIATE EXERCISE

Data 1024 (9446 – 10469) Smooth 0
Unfiltered

DURING EXERCISE

Data 1024 (22504 – 23527) Smooth 0
Unfiltered

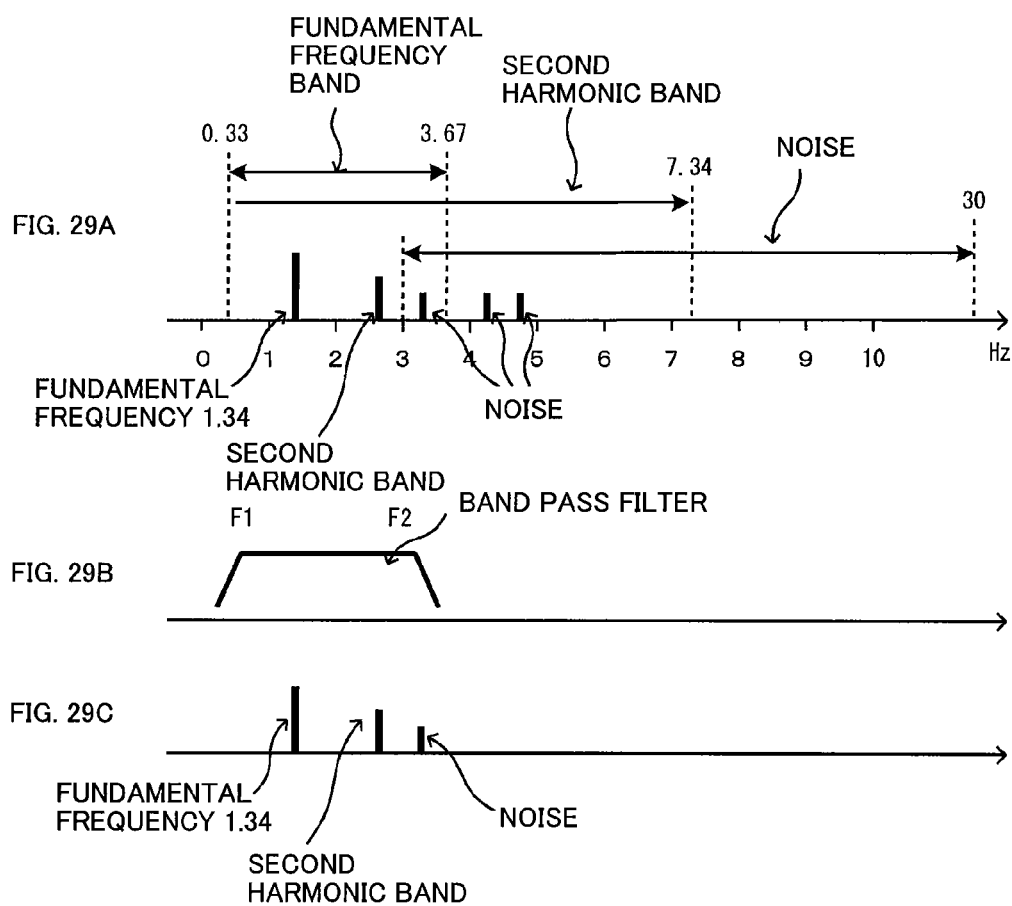

DURING EXERCISE

HEART RATE METER AND HEART BEAT DETECTING METHOD

TECHNICAL FIELD

The present invention relates to a heart rate meter and a heart beat detecting method, and more particularly, it relates to a method for removing noise such as motion artifact and disturbance noise, being included in a heart beat waveform.

BACKGROUND ART

Conventionally, various heart rate meters have been suggested for measuring a heart rate of a living body. By way of example, the patent document 1 is known as disclosing a pulse detecting circuit which irradiates a light from a light emitting device onto a body, detects a reflected light or a transmitted light therefrom by a light receiving device, and converts a received signal into a pulse signal, thereby detecting the pulse.

In using the heart rate meter as described above, it is demanded that the pulse rate is stably displayed as against noise, and there are some suggestions for enhancing the stability of the pulserate display (e.g. patent document 2, patent document 3, and patent document 4).

The patent document 2 discloses a technique which focuses attention on the point that a pulse width caused by a noise is relatively narrow, and provides a pulse wave evaluation means between a pulse wave detecting circuit and a pulse wave operation means for evaluating the pulse width of pulse signals outputted from the pulse wave detecting circuit. With the pulse wave evaluation means, only a signal evaluated as a normal pulse wave signal is transferred to the pulse wave operation means, and thereby obtaining a stability in displaying the pulse.

The patent document 3 discloses a technique to remove a body motion by using an acceleration sensor and wavelet transformation. In this document, it is disclosed as the following: the acceleration sensor detects a body motion waveform assuming the body motion as an acceleration, and the body motion waveform is subjected to the wavelet transformation to generate body motion analytical data for each frequency domain; in addition, a pulse waveform detected from a detection target part of the living body is subjected to the wavelet transformation to generate pulse wave analytical data for each frequency domain; and the body motion analytical data is subtracted from the pulse wave analytical data, so as to detect a pulse.

The patent document 4 also discloses that in the photoplethysmography (PPG) for optically detecting heart rate information, a noise being a high frequency component, is removed from a PPG signal by using the wavelet transformation.

Patent document 1: Japanese Examined Patent Application Publication No. 61-29730
Patent document 2: Japanese Examined Patent Application Publication No. 04-79250
Patent document 3: Japanese Unexamined Patent Application Publication No. 11-9564
Patent document 4: Japanese Examined Patent Application Publication No. 2003-310562
Non-patent document 1: "Exercise Physiology for Health and Physical Fitness", pp. 75 to 78, Author: Toshihiro Ishikawa, Professor emeritus, Juntendo University, published by Kyorin-shoin, April 2000

DISCLOSURE OF THE INVENTION

Problems to be Solved by the Invention

A heart rate is measured by a heart rate meter under various measuring conditions, such as during non-exercise and during exercise. As to the heart beat waveforms detected by the heart rate meter under such various conditions, there are various signal properties such as a frequency and a crest value, not only in a basic waveform but also in a noise component superimposed thereon.

FIG. 24 shows an example of a heart beat waveform that is detected by a heart rate detecting unit such as the heart beat sensor. A fundamental wave and a higher harmonic constitute primary component of the heart beat waveform. In addition to the primary component, a noise component is superimposed thereon, and the heart beat waveform includes a large number of frequency components.

By way of example, the basic waveform may contain the higher harmonic like the second harmonic, in addition to a fundamental frequency component. The noise component may include a disturbance noise being an electrical high frequency noise, which breaks into the heart beat sensor and a transmission system, and further includes a motion artifact being a micro vibration generated due to a positional displacement of a mounting point of the heart beat sensor, which occurs when a person to be measured with the heart beat sensor mounted thereon performs exercise.

FIG. 25 illustrates examples of the noise component included in the heart beat waveform as shown in FIG. 24. FIG. 25A illustrates an example of the disturbance noise, and FIG. 25B illustrates an example of the motion artifact.

The frequency and the crest value of the fundamental wave and the higher harmonic vary depending on the condition under which the person to be measured uses the heart rate meter, and various characteristics are shown under each of the conditions, for example, non-exercise state, exercise initiation state, and during-exercise state.

FIG. 26, FIG. 27, and FIG. 28 illustrate the frequency characteristics, respectively, in the non-exercise state, the exercise initiation state, and during-exercise state. As described above, the heart beat waveform includes the disturbance noise and the motion artifact in addition to the primary component such as the fundamental wave and the higher harmonic like the second harmonic, in each of the states. During exercise, the frequency of the fundamental wave and the second harmonic becomes higher than the frequency in the non-exercise state, as well as lower frequency components are increased (see FIG. 28). In the state of exercise initiation, higher frequency components are increased, compared to the primary component of the fundamental wave and the higher harmonic such as the second harmonic (see FIG. 27).

Here, it is to be noted that the heart rate of a human body is approximately 20 to 220 bpm (heart beats per minute), and the fundamental frequency in this state falls into the frequency band of 0.33 (=20 bpm/60 sec) to 3.67 (=220 bpm/60 sec) Hz. If a higher harmonic up to the second harmonic is considered, it falls into the frequency band of 0.33 (=20 bpm/60 sec) to 7.34 (3.67×2) Hz. The non-patent document is taken as an example, as the document describing the heart rate. The non-patent document describes the heart rate during exercise as a relational expression; Maximum heart rate during exercise=220−Age. That is, 220 bpm is set as the upper limit. On the other hand, as for the lower limit, the non-patent document 1 describes that there is a known example of the lowest actual measured value of a ski player who shows the heart rate of 28 bpm in resting state.

In general, in the non-exercise state, the heart rate is a low value, for instance, not higher than 80 bpm, and the fundamental frequency is not higher than 1.34 Hz with small amplitude. The non-patent document discloses actual measured data showing that in the non-exercise state, 90% or more of the measured persons have the heart rate that falls into the range of 50 to 80 bpm. On the other hand, during exercise, the heart rate becomes higher than 80 bpm, as well as the fundamental frequency becomes higher, and in addition, the signal amplitude increases, for instance at least 1.5 times or more, according to the blood flow being increased by the exercise.

In order to remove the noise component included in the heart beat waveform, it is generally considered to extract signal components within the frequency band that contains the primary component, by using a band pass filter, or the like, which has a predetermined frequency bandwidth as a passband.

FIG. 29 illustrates an example of the non-exercise state (assuming the fundamental frequency as 1.34 Hz), and FIG. 30 illustrates an example during exercise (assuming the fundamental frequency as 3.0 Hz). These examples illustrate that the noise is removed by the band pass filter having the passband of 0.33 (20 bpm/60 sec) to 3.67 (=220 bpm/60 sec) Hz.

As described above, the heart rate of a human body has a frequency band of the primary component, from 0.33 (20 bpm/60 sec) to 3.67 (=220 bpm/60 sec) Hz, the frequency components of the heart beat waveform (FIG. 29A and FIG. 30A) are made to pass through the band pass filter having the passband of 0.33 (20 bpm/60 sec) to 3.67 (=220 bpm/60 sec) Hz, and thereby it is possible to extract the fundamental frequency and its second harmonic as the primary component of the heart beat waveform. For example, in the non-exercise state, the fundamental frequency (1.34 HZ) and its second harmonic (2.67 Hz) can be extracted (FIG. 29C), and during exercise, the fundamental frequency (3.0 Hz) can be extracted (FIG. 30C).

However, since the frequency band of the noise component is from 3 to 30 Hz, there exists an overlapping part in the frequency band (e.g., 3.0 Hz to 3.67 Hz) between the frequency band of the primary component and the frequency band of the noise component in the heart beat waveform. Therefore, it is a problem that if there is a noise component in the overlapping part of the frequency part, this noise component cannot be removed (e.g., the noise component in FIG. 29C).

As described above, if the noise included in the heart beat waveform is removed, by the signal processing that extracts a signal component in the frequency band where the primary component is included and removes the signal component in the other frequency band, there is a problem that the noise component existing within the extracted band cannot be removed. Similar problems are found not only in the processing by the band pass filter as described above, but also in another method according to a frequency analysis such as using the aforementioned wavelet transformation.

Furthermore, as shown in FIG. 30, since the noise component having a lower frequency increases during exercise, it is not possible to remove the noise component which is generated within the passband of the band pass filter (FIG. 30C). During the exercise, the fundamental frequency becomes higher, and accordingly, the second harmonic goes out of the passband of the band pass filter. Therefore, the second harmonic is removed and the primary component includes only the fundamental frequency. As thus described, during exercise, the noise component remains and the primary component only includes the fundamental frequency, resulting in that a problem occurs, i.e., S/N ratio is deteriorated.

As discussed above, since the variation of the measuring condition may cause various signal properties such as the frequency and the crest value of the fundamental wave, higher harmonic, and noise component, there is a problem that it becomes more difficult to remove the noise component for effectively detecting the primary component included in the heart beat waveform, and therefore, an accurate detection of the heart rate is hampered.

In view of the situation above, an object of the present invention is made to solve the conventional problems, and it is directed to accurately detecting a heart rate, even when the variation of the measuring condition causes various signal properties, such as the frequency and the crest value of the fundamental wave, higher harmonic, and noise component, which are included in the heart beat waveform.

Means to Solve the Problems

The present invention is directed to a heart rate meter including a heart beat waveform detecting unit for detecting a heart beat waveform of a living body, and a signal processor for detecting a heart beat from the heart beat waveform.

The signal processor includes a heart beat signal generating processor for subjecting the heart beat waveform to a signal processing to generate a heart beat signal, and a heart beat detecting processor for detecting a heart beat from the heart beat signal generated by the heart beat signal generating processor.

The heart beat signal generating processor according to the present invention performs the signal processing for adding a predetermined frequency characteristic, and thereby generating a heart beat signal in which a signal intensity of a frequency component is amplified. This amplification of the signal intensity of the frequency component increases the primary component of the heart beat waveform, and reduces a noise component.

The heart beat signal generating processor includes a signal amplifier for amplifying a signal of a frequency component of the heart beat waveform. This signal amplifier amplifies the frequency component in a lower band of the heart beat waveform at low gain, and amplifies the frequency component in a higher band at high gain. Accordingly, a predetermined frequency characteristic is added to the heart beat waveform, and thereby increasing the primary component of the heart beat waveform and reducing the noise component. In this signal processing, for instance, the frequency component of the heart beat waveform is subjected to the signal amplification according to a differential property.

In addition, the heart beat signal generating processor is able to include a band pass filtering process. With this configuration, a signal within a predetermined narrow band of the heart beat waveform is subjected to the signal processing, thereby removing the noise component in the frequency band other than the primary component of the heart beat waveform.

The signal processing for removing the noise component and amplifying the signal intensity, which is performed in the heart beat signal generating processor, adds a waveform distortion to the heart beat signal. The waveform distortion according to the present invention increases the primary component of the heart beat waveform, and reduces the noise component. Accordingly, a strong correlation is generated between the waveform distortion and the heart beat. Therefore, this waveform distortion provides heart beat information with a preferable S/N ratio.

The heart beat detecting processor according to the present invention detects the waveform distortion added to the heart beat signal by the heart beat signal generating processor, whereby noise effects are reduced and the heart beat can be detected without any error.

It is to be noted that a heart beat sensor and a detecting circuit can constitute the heart beat detecting unit. By way of example, an optical reflection sensor or a transmission sensor may serve as the heart beat sensor. If the heart beat sensor outputs an optical signal, the detecting circuit converts the optical signal into an electrical signal, and subjects the signal to the signal amplification as appropriate.

The heart beat signal generating processor according to the present invention performs a narrowband signal processing that subjects a predetermined frequency band within the frequency provided in the heart beat signal to a signal processing.

The heart beat signal generating processor includes a band pass filter through which the frequency component in the predetermined narrow band out of the frequency component of the heart beat waveform is made to pass, and either of the disturbance noise component and the motion artifact component, or both the disturbance noise component and the motion artifact component are removed, and a signal amplifier for amplifying the frequency component that passed through the band pass filter, at high gain on the high-frequency side.

The band pass filter removes the noise component in the frequency band other than the primary component of the heart beat waveform. The passband of the band pass filter has a frequency range as the following; a frequency not lower than the frequency of the second harmonic of the highest heart beat waveform in the first state of heart beat is assumed as a cutoff frequency in the higher band. In addition, a frequency not higher than the fundamental frequency of the lowest heart beat waveform in the first state of heart beat is assumed as a cutoff frequency in the lower band.

The signal amplifier performs the amplification by emphasizing the frequency component on the higher frequency side, according to the amplification based on the differential property, for instance. The differential property may be a first order differential property or a second order differential property, and it may be another differential property having a higher order. However, considering the S/N ratio of the heart beat waveform, the hardware configuration forming the signal processor, and the cost-benefit performance thereof, the second order differential property is appropriate, which allows the gain of 40 dB. According to the differential property such as the second order differential property, the frequency component on the high-frequency side of the heart beat signal is emphasized and amplified.

The signal amplifier is provided with an amplification characteristic that maximizes the amplification degree around the fundamental frequency of the highest heart beat waveform in the second state of heart beat, and the component around this frequency is more emphasized and amplified. Accordingly, the noise component is amplified at low gain, and the component of the fundamental frequency and the second harmonic of the heart beat are amplified at high gain, whereby the effect of the noise is reduced.

The amplification characteristic of the signal amplifier is provided with a frequency band where the gain is lowered gradually, in the frequency range where the frequency is higher than the frequency at the highest amplification degree. With this configuration, even when the frequency of the second harmonic fluctuates, the signal component can be effectively acquired without missing any of the signal components, and it is further possible to capture another harmonic component having a higher order.

Therefore, the heart beat signal generating processor of the present invention is provided with a frequency characteristic which combines the followings: the frequency range assuming the frequency not higher than the fundamental frequency of the lowest heart beat waveform in the first state of heart beat as a cutoff frequency in the lower band and assuming the frequency not lower than the second harmonic of the highest heart beat waveform in the first state of heart beat as a cutoff frequency in the higher band; and the amplification characteristic that maximizes the amplification degree around the frequency of the fundamental frequency of the highest heart beat waveform in the second state of heart beat.

In the frequency characteristic as described above, the frequency range is set by the frequency that is determined by the first state of heart beat. The first state of heart beat is assumed as a state where the heart rate is low and therefore the fundamental frequency is low, and the second state of heart beat is assumed as a state where the heart rate is high and therefore the fundamental frequency is high. Furthermore, it is assumed that the primary component of the heart beat waveform indicates the fundamental frequency and the second harmonic.

Here, it is to be noted that there is a certain range as to the frequency, which can be taken in the first state, and the fundamental frequency and the second harmonic of the heart beat waveform may fluctuate within a given frequency range depending on a measuring target and a measuring condition.

Within the frequency range, the frequency not higher than the fundamental frequency of the lowest heart beat waveform is assumed as the cutoff frequency in the lower band, whereby it is possible to set the frequency that is conceivable to be the lowest in the low frequency including the primary component, as a standard of the frequency on the lower band.

Similarly, within this frequency range of the fundamental frequency and the second harmonic frequency, the frequency not lower than the frequency of second harmonic of the highest heart beat waveform is assumed as the cutoff frequency on the higher band, whereby it is possible to set the frequency that is conceivable to be the highest in the high frequency including the primary component, as a standard of the frequency on the higher band.

Therefore, this passband indicates a frequency band having an extended range, including frequencies as standards; the fundamental frequency of the lowest heart beat waveform and the frequency of the second harmonic of the highest heart beat waveform.

Since the frequency range is set as described above, if a frequency component within this frequency range is detected out of the frequency components of the heart beat waveform, this frequency component always includes the primary component of the heart beat; the fundamental frequency or the second harmonic, and therefore, it is possible to obtain a heart beat signal from the primary component being detected.

On the other hand, in the aforementioned frequency characteristic, the amplification characteristic amplifies the frequency component on the high-frequency side, in a scale larger than the frequency component on the low-frequency side, and the amplification degree is rendered to be the highest around the fundamental frequency of the highest heart beat waveform in the second state of heart beat. The second state of heart beat is set to have a high heart rate per unit time and a high fundamental frequency, whereby amplification at a high degree can be performed for the fundamental frequency component that is conceivable as the highest in the high frequency band which includes the primary component.

By setting the amplification characteristic as described above, even when the fundamental frequency becomes high in the second state, the second harmonic goes out of the aforementioned frequency range, and the fundamental frequency becomes only the primary component of the heart beat waveform included in the frequency range, the fundamental frequency can be amplified with reliability and the signal thereof can be amplified on a larger scale, compared to the signals of the other frequencies. Therefore, the S/N ratio of the heart beat information can be enhanced, enabling acquisition of the heart beat signal from the detected primary component.

It is possible to assume that the first state of heart beat is non-exercise state, and the second state of heart beat is during-exercise state.

In the aforementioned heart beat signal generating processor performs the amplification process by emphasizing the frequency component on the high-frequency side, and therefore, a heart beat signal being generated has an emphasized slope component. Since the slope component is generated based on the primary component of the heart beat waveform, the number of the slope parts corresponds to the number of heart beats. The heart beat detecting processor according to the present invention detects this slope component, and thereby the heart beat is detected.

The heart beat detecting processor according to one aspect of the present invention detects a waveform slope component of the heart beat signal, and when it coincides with a predetermined waveform slope component, a heart beat is detected. It is to be noted that any of the signal variation during the rise time of the heart beat signal waveform and the signal variation during the fall time thereof may be employed as the slope component. Alternatively, both of the signal variations may be employed. In this case, since the detected result becomes twice as large as the heart rate, the detected value is made half to obtain the heart rate.

The heart beat detecting processor according to another aspect of the present invention is provided with a waveform distortion detecting unit for detecting a waveform distortion that is added to the heart beat signal, using a crest value and inclination of a heart beat signal as a detecting condition. This waveform distortion detecting unit detects the waveform distortion as a heart beat.

Here, the detecting condition includes that the heart beat signal has a predetermined crest value or higher, and the inclination of the heart beat signal shows a monotonous increase or a monotonous decrease within a predetermined period, or alternatively, it shows both the monotonous increase and the monotonous decrease.

The predetermined crest value may be a frequency component around the frequency of the second harmonic of the highest heart beat waveform of the heart beat during non-exercise. In general, the crest value of the fundamental frequency of the heart beat waveform is higher than the crest value of the second harmonic. In addition, the crest value during exercise becomes higher than the crest value during non-exercise. Further in general, the crest value of the second harmonic of the heart beat waveform is higher than the crest value of the noise component in many cases.

In view of the situation above, it is possible to determine the presence or absence of the primary component of the heart beat waveform, by setting a detecting condition in which the crest value higher than the frequency component around the frequency of the second harmonic during non-exercise time is detected.

It is further possible to set the predetermined period to be a period range not longer than a quarter of the heart beat waveform period. If the primary component of the heart beat waveform includes at least the fundamental frequency and the second harmonic, the period characteristic thereof is assumed as a quarter of the heart beat waveform at the longest. Therefore, the primary component of the heart beat is increased monotonously or decreased monotonously during at least the period range of not longer than a quarter of the heart beat waveform period. This period range corresponds to the width of the aforementioned slope part.

Here, if a heart beat signal is obtained by sampling the heart beat waveform, successive sampling points are detected, the number of which corresponds to the value obtained by the following computation; the time range being a quarter of the heart beat waveform is divided by the sampling period. Then, when the values of the sampling points are larger than the frequency component around the frequency of the second harmonic of the highest heart beat waveform during non-exercise, and the values increase monotonously or decrease monotonously, the waveform distortion is detected as a heart beat.

In addition to the aforementioned aspect of the heart rate meter, the present invention includes another aspect directed to a method for removing a noise of the heart beat waveform and detecting a heart beat.

The heart beat detecting method includes a heart beat waveform detecting step for detecting a heart beat waveform of a living body, a heart beat signal generating step for subjecting the heart beat waveform to a signal amplification processing to generate a heart beat signal in such a manner that frequency component in a lower band of the heart beat waveform is amplified at low gain and the frequency component in a higher band of the heart beat waveform is amplified at high gain, a waveform distortion detecting step for detecting a waveform distortion that is added to the heart beat signal in the heart beat signal generating step, and a heart beat detecting step for detecting a heart beat from the waveform distortion.

In the heart beat signal generating step, the signal amplification processing subjects the frequency component of the heart beat waveform to the signal amplification according to a differential property, and the heart beat detecting step detects the waveform distortion, thereby allowing a detection of a fundamental wave or a second harmonic of the heart beat waveform, or both the fundamental wave and the second harmonic, as the heart beat.

Here, one aspect of the heart beat signal generating step includes two processes of narrowband signal processing, including: a band pass processing that allows passage of the frequency component in a predetermined narrow band out of the frequency component of the heart beat waveform, so as to remove a disturbance noise or a motion artifact, or both the disturbance noise and the motion artifact; and a signal amplification processing for subjecting the frequency component in the narrow band to the signal amplification according to the differential property such as a second-order differential property, which amplifies signals on the high-frequency side at a high amplification degree.

In another aspect of the heart beat signal generating step, the band pass processing is performed with a restriction of a frequency range, assuming the frequency not higher than the fundamental frequency of the lowest heart beat waveform in the first state of heart beat as a cutoff frequency in the lower band, and the frequency not lower than the frequency of the second harmonic of the highest heart beat waveform in the first state of heart beat as the a cutoff frequency in the higher band. In addition, the signal amplification processing is performed with an amplification characteristic that maximizes the amplification degree around the fundamental frequency of the highest heart beat waveform in the second state. By combining those processing above, the signal amplification is performed by emphasizing, within the frequency range, the heart beat waveform around the fundamental frequency of the highest heart beat waveform in the second state.

The band pass processing restricts the frequency range assuming the fundamental frequency of the lowest heart beat waveform measured in the non-exercise state as the lower band frequency, and assuming the fundamental frequency of the highest heart beat waveform measured in the during-exercise state as the higher band frequency.

The waveform distortion detecting step according one aspect of the present invention detects a waveform slope component of the heart beat signal and extracts a predetermined waveform slope component, whereby the noise component is removed and only the heart beat is detected.

Any of the signal variation during the rise time of the heartbeat signal waveform and the signal variation during the fall time thereof may be employed as the slope component. Alternatively, the signal variations during both the rise time and the fall time may be employed.

The waveform distortion detecting step according to another aspect of the present invention detects a waveform distortion that is added to the heart beat signal, setting the crest value and the inclination of the heart beat signal as the detecting condition, and the waveform distortion being detected is obtained as a heart beat.

Here, as described above, the detecting condition includes that the heart beat signal has a crest value being equal to or higher than a predetermined value, and the heart beat signal shows a monotonous increase or a monotonous decrease within a predetermined period, or alternatively, both the monotonous increase and the monotonous decrease; and the predetermined crest value corresponds to a frequency component around the frequency of the second harmonic of the highest heart beat waveform of the heart beat in the non-exercise state.

Effect of the Invention

According to the present invention, even when the measuring condition varies and there are changes in the signal properties such as the frequencies and the crest values of the fundamental wave, higher harmonic, and noise component included in the heart beat waveform, it is possible to detect an accurate heart beat.

BRIEF DESCRIPTION OF THE DRAWINGS

FIG. 20 illustrates the waveform distortion according to the fundamental frequency;

FIG. 29 illustrates an example during non-exercise (setting the fundamental frequency to 1.34 Hz)

DESCRIPTION OF THE MARKS

1 HEART RATE METER
2 HEART BEAT SENSOR
2a LIGHT EMITTING DEVICE
2b LIGHT RECEIVING DEVICE
2c LIGHT SHIELDING
2A TACTILE SENSOR
3 DETECTING CIRCUIT
3a LIGHT RECEIVING CIRCUIT
3b AMPLIFICATION CIRCUIT
3c A/D CONVERTER
4 SIGNAL PROCESSOR
5 NARROWBAND SIGNAL PROCESSOR
5a BAND PASS FILTER
5b SECOND ORDER DIFFERENTIAL PROPERTY
6 SLOPE DETECTING UNIT

6a CREST VALUE
6b SLOPE
7 HEART RATE COUNTER
8 HEART RATE NOTIFICATION UNIT
9 LIGHT EMITTING CIRCUIT
10 LIVING BODY
11 BLOOD VESSEL
12 OSCILLATORY WAVE
13 BODY TISSUE
14 SKIN
20 HEART BEAT WAVEFORM
21 FUNDAMENTAL FREQUENCY
22 SECOND HARMONIC
50 DELAY UNIT
51 COEFFICIENT MULTIPLIER
52 ADDER
60 STORING MEANS
61 FIRST COMPARATIVE MEANS
62 SECOND COMPARATIVE MEANS
63 COUNTER

BEST MODE FOR CARRYING OUT THE INVENTION

Hereinafter, a heart rate meter and a procedure for removing noise component from a heart beat waveform to detect a heart beat according to the present invention will be explained in detail, with reference to the accompanying drawings.

Figure 1:
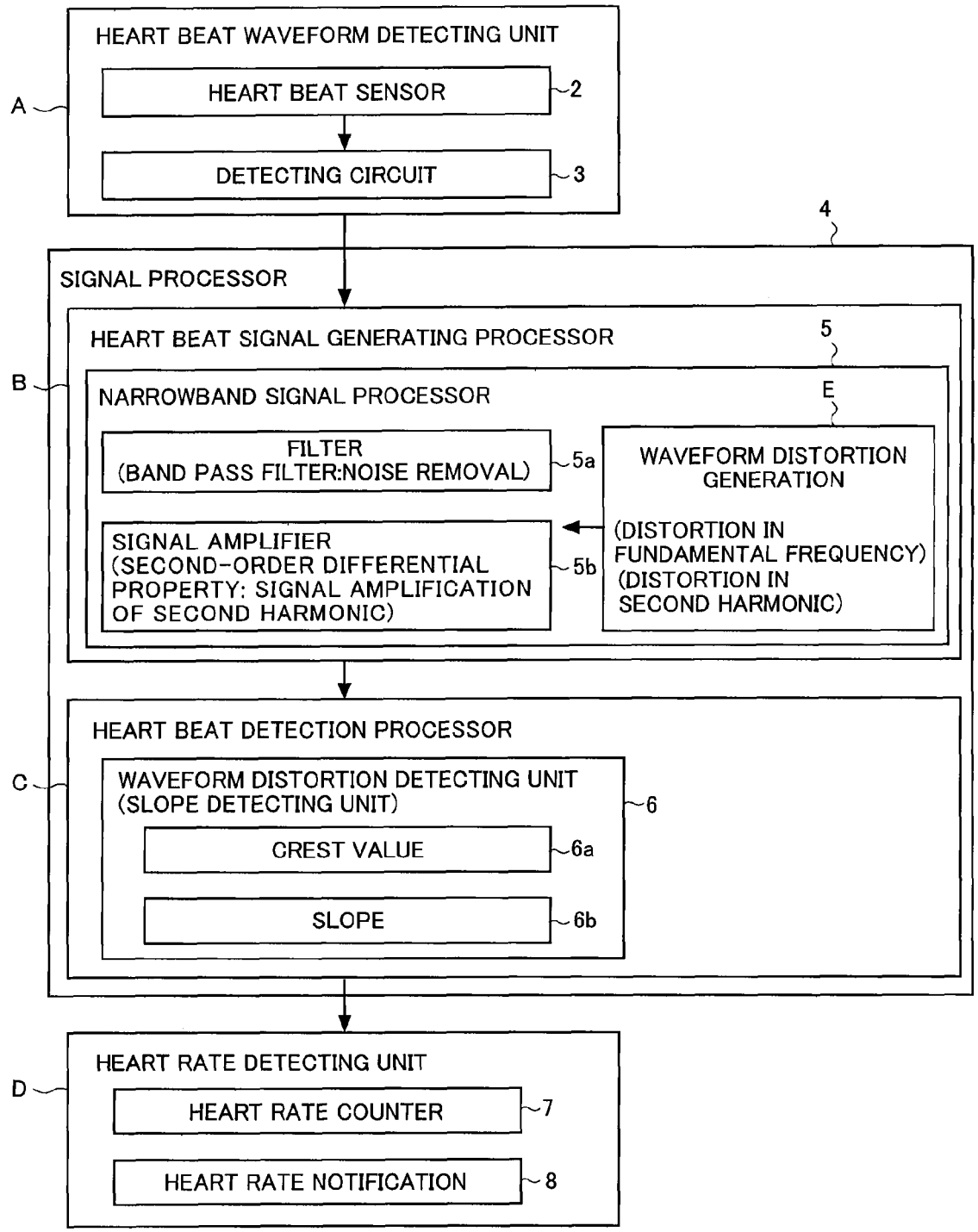
FIG. 1 is a diagram for explaining an overview of the present invention.

Firstly, an overview of the present invention will be explained with reference to FIG. 1. In FIG. 1, a heart rate meter 1 of the present invention includes a heart beat waveform detecting unit A for detecting a heart beat waveform of a living body, and a signal processor 4 for detecting the heart beat that is obtained by subjecting the detected heart beat waveform to a signal processing. Here, the signal processor 4 is provided with a heart beat signal generating processor B and a heart beat detecting processor C. A heart rate detecting unit D detects a heart rate based on the heart beat detected in the signal processor 4. Here, the heart rate detecting unit D includes a heart rate counter 7 for counting the heart rate, and a heart rate notifying unit 8 for notifying the heart rate being counted, by means of displaying, transmitting, recording, or the like.

It is to be noted here that the heart beat waveform detecting unit A may be made up of a heart beat sensor 2, and a detecting circuit 3 which acquires a detected signal from an output of the heart beat sensor 2, for instance. By way of example, an optical sensor may serve as the heart beat sensor 2, and the detecting circuit 3 converts the output such as an optical signal, acquired from the heart beat sensor 2 into an electrical signal. If necessary, the detecting circuit 3 subjects the signal to amplification, and converts the signal into a digital signal according to A/D conversion.

The signal processor 4 includes a heart beat signal generating processor B for generating a heart beat signal by subjecting signals in a predetermined narrow band of the heart beat waveform to a filtering process and a signal amplification process, and a heart beat detecting processor C for detecting a heart beat from the waveform distortion that is added to the heart beat signal, according to an addition of a predetermined frequency characteristic by the heart beat signal generating processor B.

A narrowband signal processor 5 may constitute the heart beat signal generating processor B. The narrowband signal processor 5 includes two processing contents 5a and 5b.

The first processing content 5a is to remove a noise component existing in the frequency band other than the primary component of the heart beat waveform, and the removal can be performed by extracting a signal within a predetermined narrow band from the frequency band of the heart beat waveform being captured. The heart beat waveform includes as the primary component, the frequency components of a fundamental frequency and its n-order higher harmonic. The n-order higher harmonic approaches the heart beat waveform as the larger number is taken as "n". However, in general, a crest value of the n-order higher harmonic becomes smaller as the "n" becomes larger. Therefore, if relatively low precision is sufficient, for example, in such a case of detecting a heart rate, the second order harmonic is enough, setting "2" to "n".

Figure 2A:
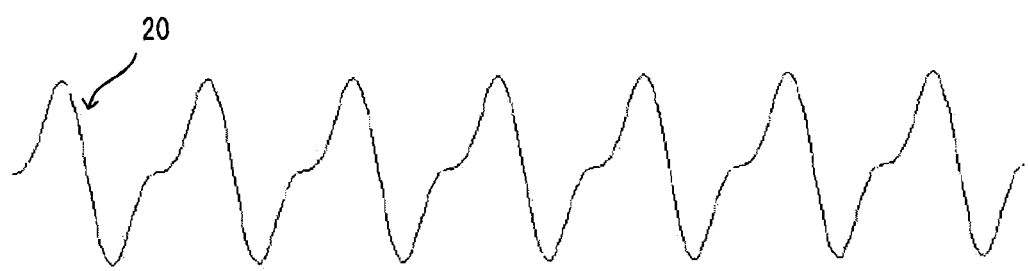
FIG. 2 illustrates an overview of a heart beat waveform, a fundamental frequency, and a second harmonic.
Figure 2B:
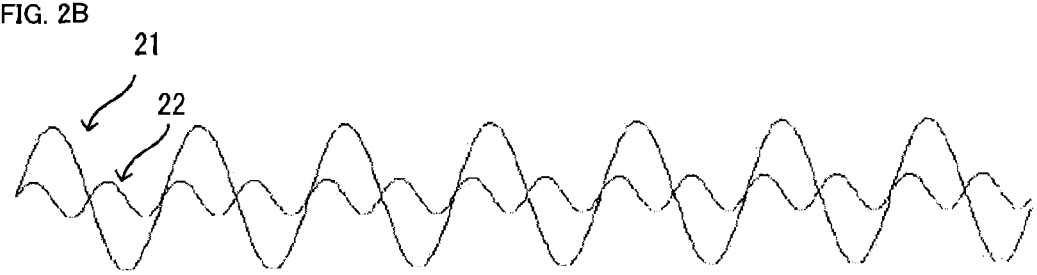

Therefore, in the example here, it is assumed that the primary component of the heart beat waveform corresponds to the frequency components of the fundamental frequency and the second harmonic. FIG. 2 illustrates an overview of the heart beat waveform, the fundamental frequency and the second harmonic. FIG. 2A shows an example of the heart beat waveform 20, and FIG. 2B shows the frequency component of the fundamental frequency 21 and the frequency component of the second harmonic 22, which are included in the heart beat waveform 20. It is to be noted here that the fundamental frequency and the second harmonic can be obtained by a frequency analysis such as Fourier transform.

On the frequency axis, there exists a frequency component caused by a noise, in addition to the frequency components of the fundamental frequency and the second harmonic as the primary component of the heart beat waveform.

The noise as described above may include a disturbance noise which breaks into the heart beat sensor or into the circuitry, and a position-indicator motion noise that is generated when the heart beat sensor is displaced from the position to be measured. The frequency included in the noise is various depending on the noise source, or the like, and such frequency appears both inside and outside the frequency range where the primary component of the heart beat waveform exists.

The narrowband signal processor 5 sets a frequency range where the frequency component of the fundamental frequency and the second harmonic as the primary component of the heart beat waveform appears, and by using this frequency range, the band of the heartbeat waveform is narrowed to generate narrowband signals which are signals only within the frequency range. By making the heart beat waveform to be a narrow band, the noise component having the frequency outside the frequency range can be removed.

By way of example, a band pass filter can implement the first processing content 5a that removes the noise component.

Next, the second processing content 5b held by the narrowband signal processor 5 is to amplify a signal intensity of the frequency component, and thereby generating a heart beat signal. This signal processing can be performed by adding a predetermined frequency characteristic to the heart beat waveform. This signal processing for adding the predetermined frequency characteristic increases the primary component of the heart beat waveform and reduces the noise component.

Even when the noise component is removed by the aforementioned narrowband signal processing, the noise component, which appears within the frequency range of the fundamental frequency and the second harmonic, is not removed but remains, causing a factor which deteriorates the S/N ratio of the heart beat signal.

The second processing of the narrowband signal processor 5 is performed to subject a crest value of the primary component to the signal amplification, as to the primary component and the noise component of the heart beat waveform, so as to enlarge a difference in signal intensity between the primary component and the noise component, whereby the S/N ratio of the heart beat signal is enhanced. In here, there is shown an example that the frequency component of the second harmonic is subjected to the signal amplification.

The second processing content 5b that subjects the crest value of the primary component to the signal amplification can be implemented, for example, by a differential property processing that mainly subjects the second harmonic to the signal amplification. The differential property processing may be a second-order differential property processing. It is to be noted here that the second-order differential property processing is one example of the differential property processing as described below. In addition, the differential property processing is also an example for performing the signal amplification at high gain in a high frequency domain.

The removal of the noise component and the amplification of the signal intensity performed in the narrowband signal processing 5 may add a waveform distortion to the heart beat signal (E in FIG. 1). The signal intensity amplification performed in the narrowband signal processing 5 subjects the frequency component of the primary component, in particular, the fundamental frequency and the second harmonic, to non-linear signal amplification. Therefore, the intensity ratio of the frequency component included in the heart beat signal obtained by this signal amplification becomes different from the intensity ratio of the frequency component included in the original heart beat waveform. This means that a waveform distortion is added to the heart beat signal.

According to this waveform distortion, the heart beat waveform is distorted from the original signal form. Since the primary component of heart beat waveform is increased and the noise component is reduced, the waveform distortion achieves a stronger correlation with the heat beat, rather than the heart beat waveform. Therefore, by detecting the waveform distortion obtained by the narrowband signal processing 5, the heart beat information can be obtained at a preferable S/N ratio.

Detailed example of the narrowband signal processing according to the band pass filter and the second-order differential property processing will be explained below with reference to FIG. 7.

A waveform distortion detecting unit 6 may constitute the heart beat detecting processor C. The waveform distortion detecting unit 6 detects a predetermined slope component included in the heart beat signal, for instance, and detects a heart beat by associating this slope with the heart beat. The slope component may be obtained either from a signal variation during the rise time of the heart beat signal waveform or from a signal variation during the fall time. Alternatively, it may be obtained from the signal variations in both of the rise time and the fall time.

The waveform distortion detecting unit 6 detects the waveform distortion added to the heart beat signal, setting the crest value 6a and the slope 6b of the heart beat signal as a detecting condition.

The detecting condition includes that the heart beat signal shows a predetermined crest value or higher, and the slope of the heart beat signal shows a monotonous increase or a monotonous decrease within a predetermined period of time, or alternatively, both the monotonous increase and the monotonous decrease.

The predetermined crest value may be a frequency component, for example, around the frequency of the second harmonic of the highest heart beat waveform of the heart beat during non-exercise.

As for the heart beat waveform, in general, the crest value of the fundamental frequency of the heart beat waveform is higher than the crest value of the second harmonic, and the crest value during exercise is higher than the crest value during non-exercise. Furthermore, in many cases, the crest value of the second harmonic of the heart beat waveform is higher than the crest value of the noise component.

In view of above situation, the primary component of the heart beat is detected, setting the crest value as the first condition. By setting the crest value of the frequency component around the frequency of the second harmonic during non-exercise as a threshold value, there is a possibility that the frequency component smaller than this crest value does not include the primary component of the heart beat, and the frequency component larger than the crest value includes the primary component.

However, the frequency component of the noise component may goes over the aforementioned crest value depending on the size. Therefore, it is not possible to detect the primary component of the heart beat, just by determining the primary component of the heart beat waveform based on the crest value.

Given the situation above, the slope during a predetermined period of time is set as the second condition to detect the primary component of the heart beat. If the primary component of the heart beat waveform includes at least the fundamental frequency and the second harmonic, it is assumed that the period characteristic of the primary component is a quarter of the period of the heart beat waveform at the longest. In this case, the primary component of the heart beat increases monotonously or decreases monotonously during at least the period range of not longer than a quarter of the heart beat waveform period.

Therefore, the heart beat is detected, setting the condition of the slope, in such a manner that the signal monotonously increases or monotonously decreases in a predetermined period, the period having a width not longer than a quarter of the heart beat waveform period.

If the heart beat signal is sampling data, successive sampling points are obtained, the number of which corresponds to the value that is calculated by dividing the duration of time being one quarter of the heart beat waveform period, by the sampling period. If the values of the sampling points are larger than the frequency component around the frequency of the second harmonic of the highest heart rate waveform as to the heart beat during non-exercise, and the values of the sampling points show monotonously increase or monotonously decrease, this heart beat signal is detected as the heart beat.

Next, with reference to FIG. 3, a schematic configuration of the heart rate meter according to the present invention will be explained. It is to be noted here that an optical sensor is illustrated as an example of the heart beat sensor 2.

The heart rate meter 1 includes a heart beat sensor 2 for acquiring heart beat information from a living body 10, a detecting circuit 3 for generating a detected signal from an output of the heart beat sensor 2, a signal processor 4 for subjecting the detected signal from the detecting circuit 3 and detecting a heart beat, a heart rate counter 7 for counting a heart rate, and a heart rate notification unit 8 for notifying the heart rate being counted.

Figure 4:
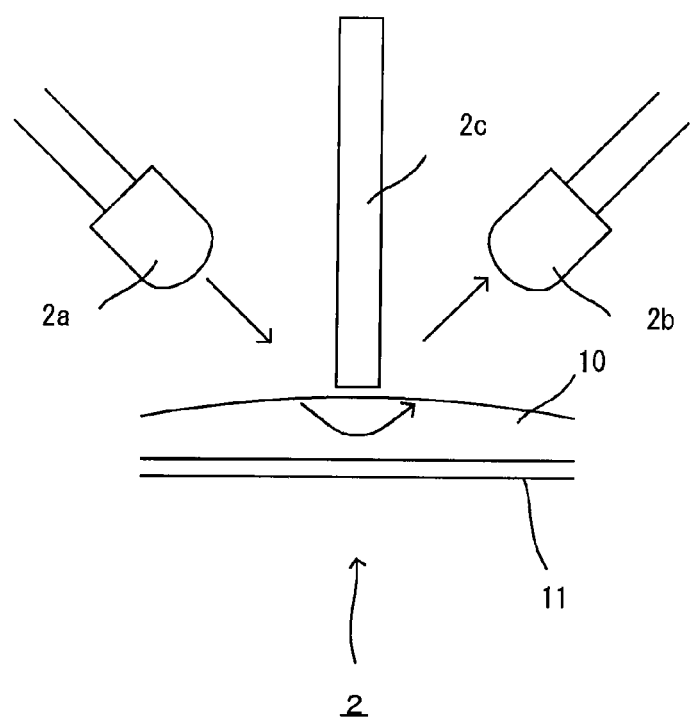
FIG. 4 is a schematic sectional view for explaining one configuration example of a heart beat sensor.

The heart beat sensor 2 is provided with a light emitting device 2a driven by the light emitting circuit 9 for irradiating light on the living body 10, and a light receiving device 2b for receiving the light that is scattered or reflected, or transmitted from the living body 10. FIG. 4 shows a schematic sectional view for explaining one configuration example of the heart beat sensor 2, and shows the configuration example for irradiating light against the living body 10, and detecting the light being reflected. The light emitting device 2a and the light receiving device 2b are opposed to each other placing a shielding plate 2c therebetween, and they are located in a manner being symmetrical with respect to an irradiated point (not illustrated). Here, the shielding plate 2c blocks the light that is directly incident from the light emitting device 2a to the light receiving device 2b.

The light irradiated from the light emission device 2a onto the living body 10 is scattered by the tissue in the living body 30 and the blood in the blood vessel 11, and emitted outwardly from the living body 10. The intensity of the light emitted from the living body 10 fluctuates according to a blood stream. The heart rate meter 1 according to the present invention detects the heart beat based on the variation of the light intensity that fluctuates according to the blood stream.

The detecting circuit 3 includes a light receiving circuit 3a which receives the optical signal obtained from the light receiving element 2b and converts the signal into a detected signal being an electrical signal, an amplifier circuit 3b which subjects the detected signal to signal amplification, and an A/D converter 3c that converts the signal into a digital signal.

The signal processor 4 includes a narrowband signal processor 5 which performs the noise removal by the aforementioned band pass filter, the second-order differential property, or the like, and signal amplification of the second harmonic, and a heart beat detecting unit (slope detecting unit) 6 for generating a waveform distortion of the heart beat signal generated by the narrowband signal processor 5 and detecting a heart beat.

The heart rate counter 7 counts a heart rate from the heart beat obtained by the signal processor 4, and the heart rate notification unit 8 notifies the heart rate counted in the heart rate counter 7. It is to be noted that this notification includes, displaying, recording, transmission, and the like, of the heart rate.

Figure 3:
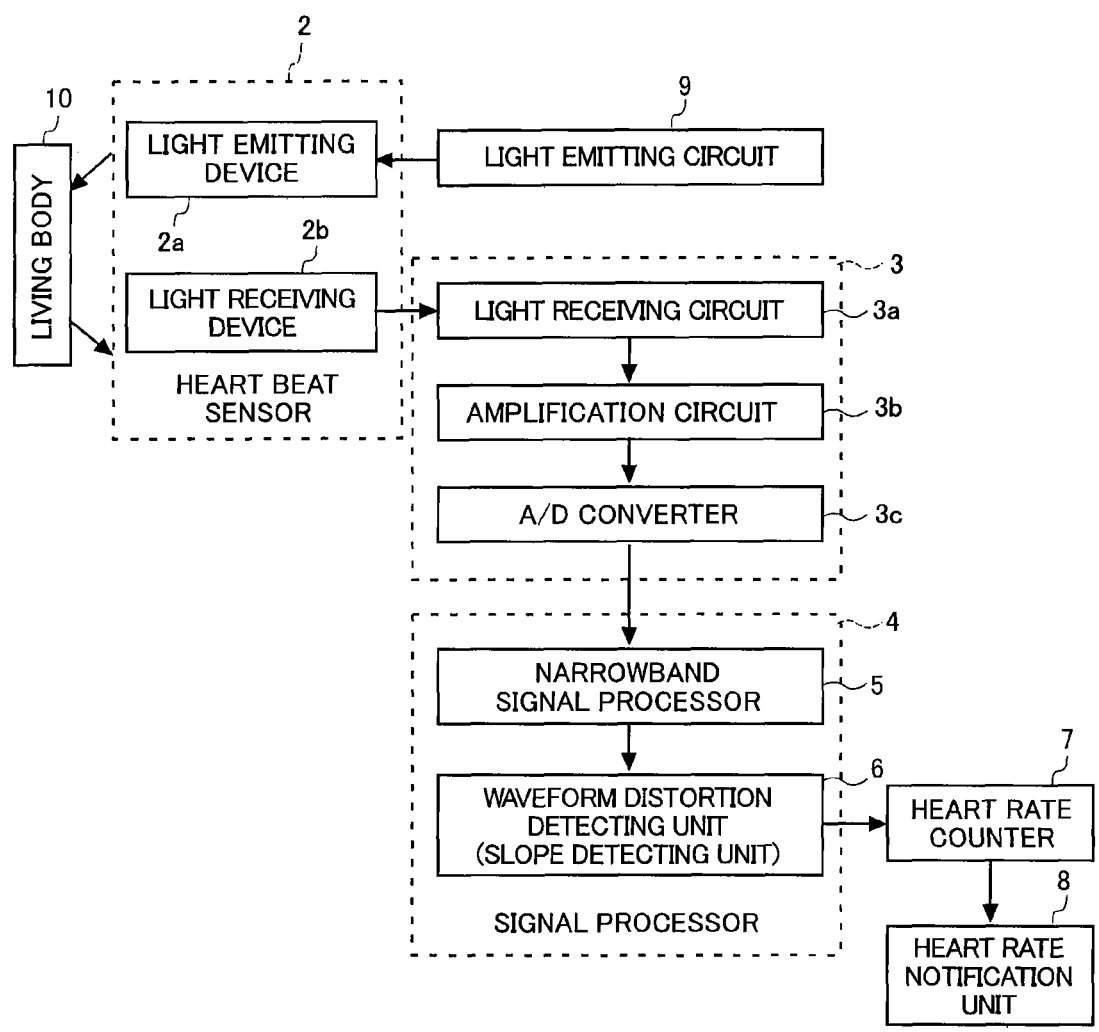
FIG. 3 is a diagram for explaining a schematic configuration of the heart rate meter according to the present invention.
Figure 5:
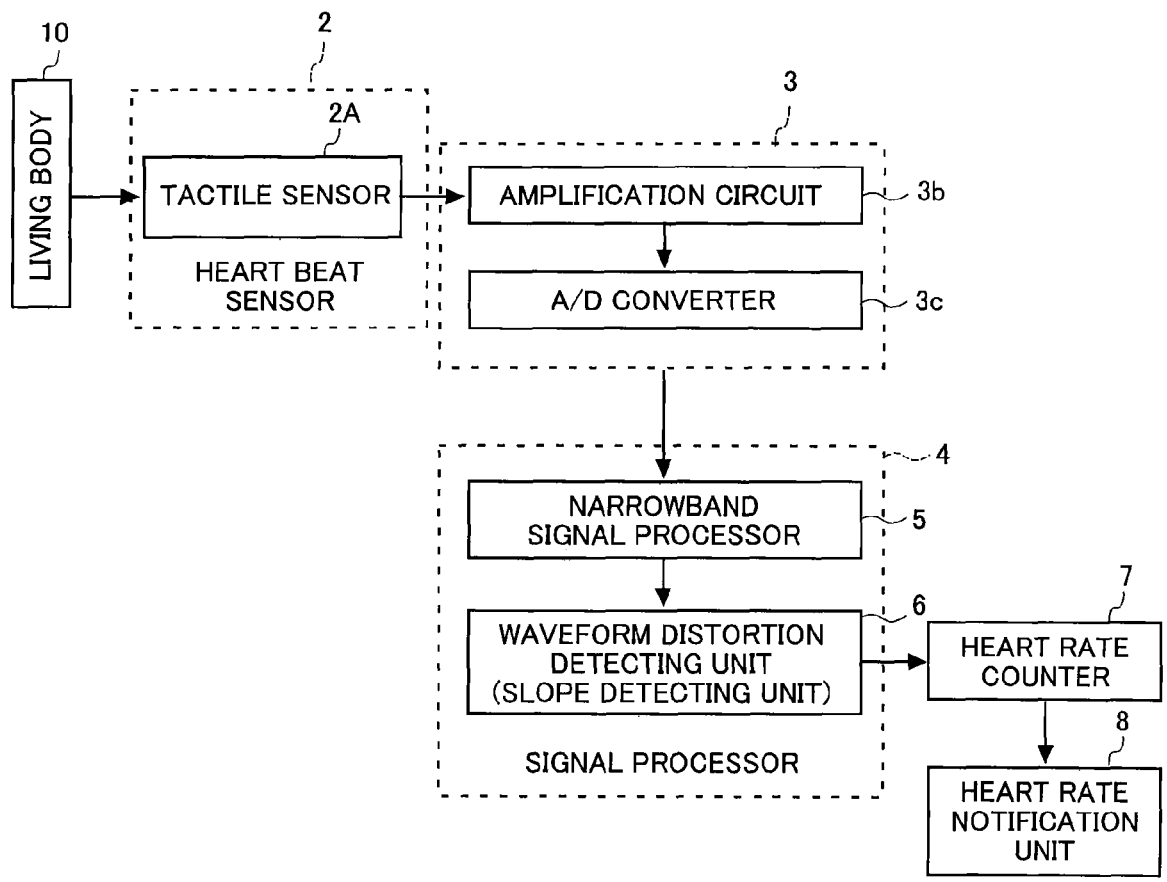
FIG. 5 is a diagram for explaining another configuration of the heart rate meter according to the present invention.

FIG. 5 is a diagram for explaining another configuration of the heart rate meter shown in FIG. 3. In this configuration, a tactile sensor 2A is illustrated as an example of the heart beat sensor 2.

The heart rate meter 1 includes, as shown in FIG. 3 described above, the heart beat sensor 2, the detecting circuit 3, the signal processor 4, the heart rate counter 7, and the notification unit 8. A detected signal from the tactile sensor 2A serving as the heart beat sensor 2 is subjected to the signal amplification by the amplifier circuit 3b in the detecting circuit 3, and converted into a digital signal by the A/D converter 3c.

In this configuration example, the tactile sensor 2A is provided as the heart beat sensor 2. Here, the tactile sensor 2A generically represents a sensor for detecting an oscillation emitted from a living body, and by way of example, this sensor detects a heart beat by detecting a pulse of arterial vessel within the living body.

Figure 6:
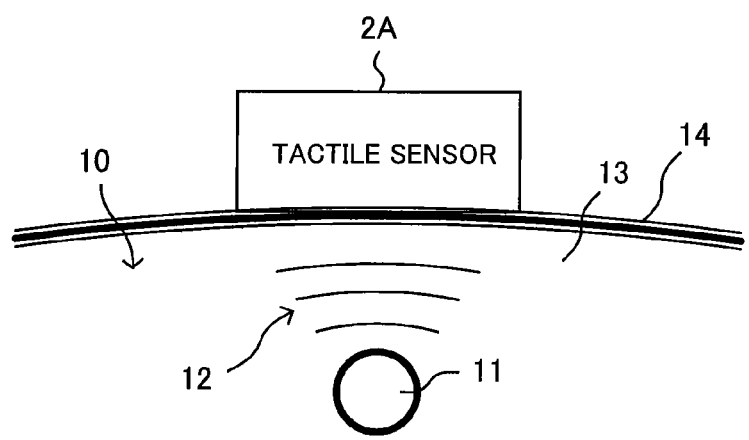
FIG. 6 is a schematic sectional view for explaining another configuration example of the heart beat sensor.

FIG. 6 is a schematic sectional view for explaining one configuration example of the tactile sensor 2A. The arterial vessel 11 within the living body oscillates, in synchronization with the pulse, according to fluctuations of the blood flowing in the blood vessel. The oscillation of the arterial vessel is propagated in the body tissue 13 in a form of oscillatory wave 12. The tactile sensor 2A is mounted on the skin, for example, in such a manner as brought into contact therewith, so as to detect the oscillatory wave 12 propagating in the body tissue 13. The oscillatory wave is detected in a form of variation of pressure or in a form of variation of oscillation.

As the tactile sensor 2A, various sensors are available depending on a manner how to detect the oscillatory wave. For example, if a pressure sensor is employed as the tactile sensor 2A, an oscillatory wave is detected as a variation of pressure. Alternatively, if an oscillation sensor is employed as the tactile sensor 2A, the oscillatory wave is detected as variation of oscillation. The variation of oscillation being detected is a variation in amplitude, frequency, or the like.

The tactile sensor 2A detects via the skin, an oscillatory wave propagating through the tissue 13 of the living body. Therefore, the tactile sensor 2A is mounted in proximity to a portion to be measured where a pulse of the living body can be detected. The detection sensitivity of the tactile sensor 2A can be improved by bringing it into contact with the skin 14 in proximity to the portion to be measured. Furthermore, by pressing the tactile sensor 2A against the skin 14, the detection sensitivity can be enhanced more.

The tactile sensor 2A detects an oscillatory wave that fluctuates according to a blood stream, the detecting circuit 3 subjects a detected signal to a signal amplification in the amplifier circuit 3b, and the A/D converter 3c converts the amplified signal into a digital signal It is to be noted here that the configuration and signal processing operations of the narrowband signal processor 5 and the waveform distortion detecting unit 6 within the signal processor 4 and the heart rate counter 7, the configuration and the signal processing of the heart rate notification unit 8, and the operations of each unit, are the same as those explained above with reference to FIG. 3. Therefore, tedious explanation will not be given here.

If an optical sensor is employed as the heart beat sensor, a portion for detecting a heart beat signal can be specified within a narrow range, and a heart beat state at a specified position can be detected. Alternatively, if a tactile sensor is employed as the heart beat sensor, a heart beat signal can be obtained from a wide range, and therefore, a high precision in deciding the position for mounting the heart beat sensor is not necessary. In addition, it is possible to reduce a faulty detection due to a displacement of the sensor while being used.

Next, with reference to FIG. 7, examples of the band pass filter and the second-order differential property will be explained, with respect to the noise component removal 5a and the signal amplification of the second harmonic 5b in the heart beat signal generating processor B.

Figure 7A:
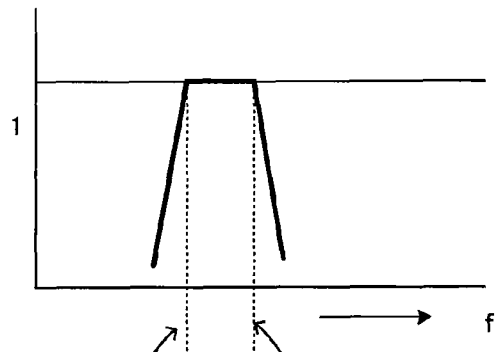
FIG. 7 illustrates details of a narrowband signal processing according to a band pass filter and a second order differential property processing.
Figure 7B:
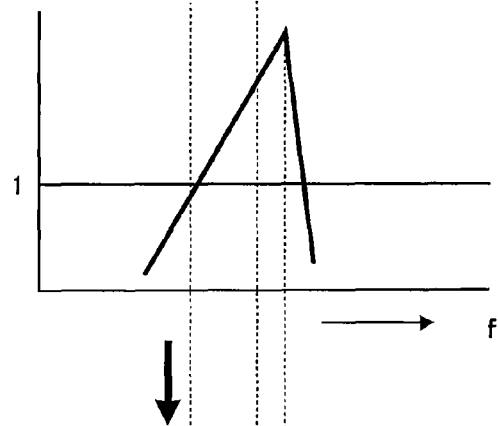
Figure 7C:
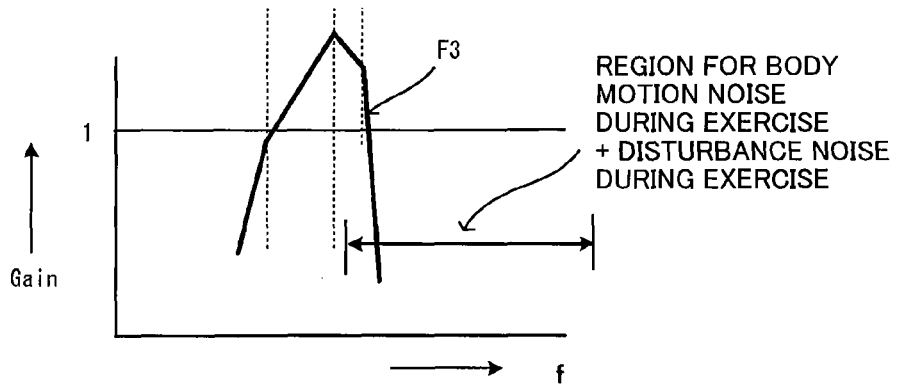

FIG. 7A shows a passband of the band pass filter, and FIG. 7B shows a frequency characteristic of the second-order differential property. FIG. 7C shows a frequency characteristic that is obtained by combining the band pass filter and the frequency characteristic of the second-order differential property.

The band pass filter is a filter which allows a passage of the frequency component in the predetermined narrow band, out of the frequency component of the heart beat waveform, and thereby either of the disturbance noise component and the motion artifact component, or both the disturbance noise component and the motion artifact component are removed.

As shown in FIG. 7A, the band pass filter sets a lower band frequency F1 as a cutoff frequency in the lower band, and the band pass filter sets a higher band frequency F2 as a cutoff frequency in the higher band.

Here, the lower band frequency F1 of the band pass filter may be set as the frequency equal to or lower than the fundamental frequency of the lowest heart beat waveform in the first state of heart beat, and the higher band frequency F2 of the band pass filter may be set as the frequency equal to or higher than the second harmonic of the highest heart beat waveform in the first state of heart beat. Here, the first state of heart beat may be assumed as non-exercise time when the person to be measured does not perform any exercise. There are individual differences in the heart rate during non-exercise, but by way of example, the heart rate may be set to 20 bpm to 80 bpm. It is to be noted that [bpm] represents the heart rate per minute. Since these heart rates respectively correspond to 0.33 Hz and 1.34 Hz. Therefore, the lower band frequency F1 may be set to 0.33 Hz and the higher band frequency F2 may be set to 2.68 Hz (1.34 Hz×2).

The second-order differential property subjects the high-frequency side to the signal amplification at a high amplification degree. As shown in FIG. 7B, the second-order differential property has an amplification degree that increases linearly from the low frequency side, directed to the high-frequency side frequency F3. The high-frequency side frequency F3 sets a differential upper limit of the second-order differentiation.

Here, the fundamental frequency of the highest heart beat waveform in the second state of heart beat may be set as the high-frequency side frequency F3 of the second-order differential property. In this case, the second state of heart beat can be assumed as the during-exercise time when the person to be measured are performing exercise. There are individual differences in the heart rate, but the heart rate can be set to 220 bpm. This heart rate corresponds to 3.67 Hz.

It is to be noted on the low frequency side, the amplification degree around the lower band frequency F1 of the band pass filter is set to be 1, approximately.

FIG. 7C shows a frequency characteristic that is obtained by combining the frequency characteristics of the band pass filter shown in FIG. 7A and the second-order differential property as shown in FIG. 7B. When examples of the frequencies of the lower band frequency F1, the higher band frequency F2, and the high-frequency side frequency F3 are set to the aforementioned numeric value examples, the frequencies become higher in the order of F1, F2, and F3. The amplification degree around the lower band frequency F1 is set to be 1 approximately. Then, the amplification degree is elevated linearly from around the lower band frequency F1, directed to the higher band frequency F2, and the amplification degree becomes the highest at the higher band frequency F2. Thereafter, the amplification degree is decreased from the higher band frequency F2 directed to the high-frequency side frequency F3, and the amplification degree becomes approximately 1 or lower in the frequency range that goes over the frequency around the high-frequency side. Also in the frequency range lower than around the lower band frequency F1, the amplification degree becomes approximately 1 or lower.

Here, the noise component (noise components such as motion artifact and disturbance noise) during exercise is approximately 3 to 30 Hz. Therefore, as shown in FIG. 7C, if the noise components are superimposed on the frequency characteristic of the aforementioned numerical values example, a major part of the noise component during exercise goes out of the passband of the band pass filter, and then removed. The noise component in proximity to 3 to 3.67 Hz within the noise component during the exercise overlaps the second-order differential property, and therefore it is not removed. As discussed above, as for the noise component that appears in this frequency range, the primary component of the heart beat waveform is emphasized and amplified by the waveform distortion detection (slope detection) of the present invention, generating a difference in crest value between the primary component and the noise component, whereby the S/N ratio is enhanced and the precision in detecting the heart beat is improved.

Since the frequency characteristic as shown in FIG. 7 is based on the aforementioned numeric value example, different frequency characteristics appear if different numeric value examples are employed. For example, a part of the frequency which indicates the highest amplification degree may be slightly deviated, but there is a common trend that the amplification degree increases from the low-frequency side to the high-frequency side.

In the frequency higher than the high-frequency side frequency F3, the gain is set in such a manner that the gain is not reduced precipitously but it is lowered gradually. Accordingly, even when the fundamental frequency and the second harmonic of the heart beat signal are displaced toward a frequency higher than the high-frequency side frequency F3, they are not cut off and can be used for detecting the heart beat. It is further possible that a third harmonic can also contribute to the heart beat detection.

Hereinafter, with reference to FIG. 8, operations according to the band pass filter and the second-order differential property in the first state of heart beat (during non-exercise) will be explained. With reference to FIG. 9, operations according to the band pass filter and the second-order differential property in the second state of heart beat (during exercise) will be explained. It is to be noted that a size ratio of each of the frequency components described below is arbitrarily set for illustrative purposes, and it does not represent the actual state.

Firstly, with reference to FIG. 8, operations according to the band pass filter and the second-order differential property in the first state of heart beat (during non-exercise) will be explained.

Figure 8A:
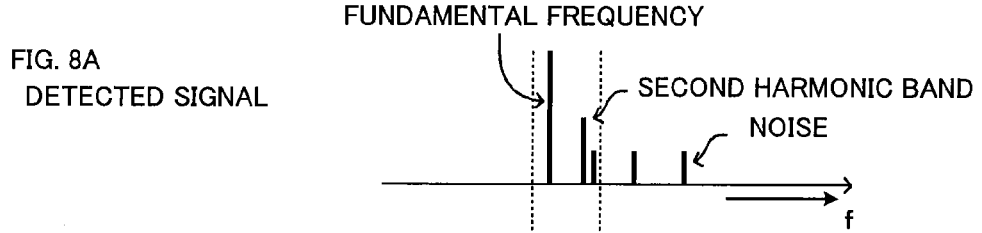
FIG. 8 illustrates operations according to the band pass filter and the second order differential property in a first state (non-exercise state) of heart beat.

FIG. 8A shows the frequency components of the detected signal (heart beat waveform) during non-exercise, and it is assumed that both of the fundamental frequency and the second harmonic exist between the lower band frequency F1 and the higher band frequency F2.

Figure 8B:
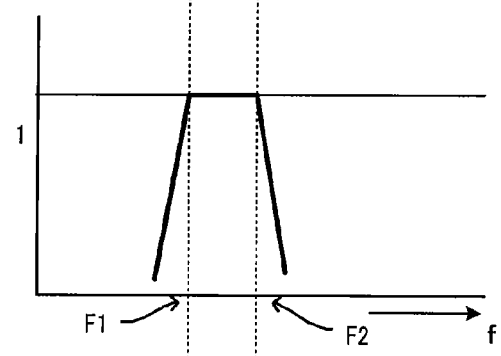
Figure 8C:
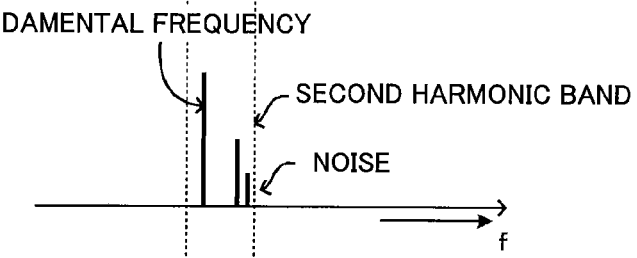

The signal shown in FIG. 8C indicates the frequency components that are obtained by allowing the frequency components shown in FIG. 8A to pass through the band pass filter as shown in FIG. 8B. According to the band pass filter, the noise components existing in a frequency domain higher than the higher band frequency F2 are removed.

Figure 8D:
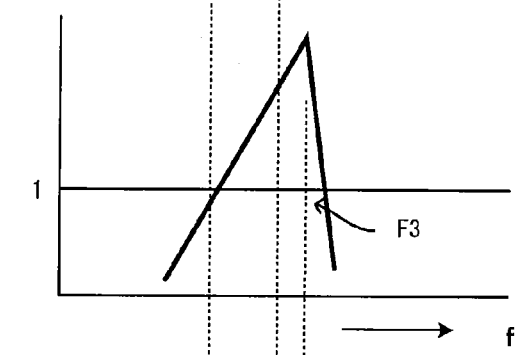
Figure 8E:
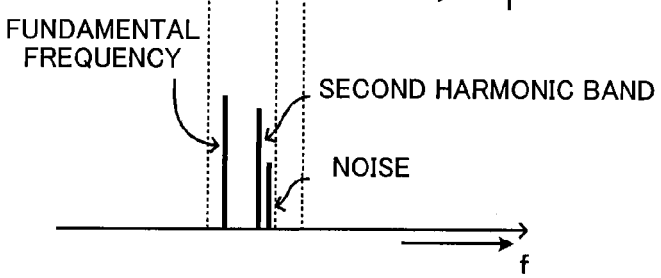

The signal as shown in FIG. 8E represents the frequency components that are obtained by subjecting the signal after passing the band pass filter to the signal amplification according to the second-order differential property as shown in FIG. 8D. According to the second-order differential property, the frequency component around the higher band frequency F3 is amplified more drastically. In FIG. 8D, the frequency component of the second harmonic and the noise component are emphasized and amplified.

Next, with reference to FIG. 9, operations according to the band pass filter and the second-order differential property in the second state of heart beat (during exercise) will be explained.

Figure 9A:
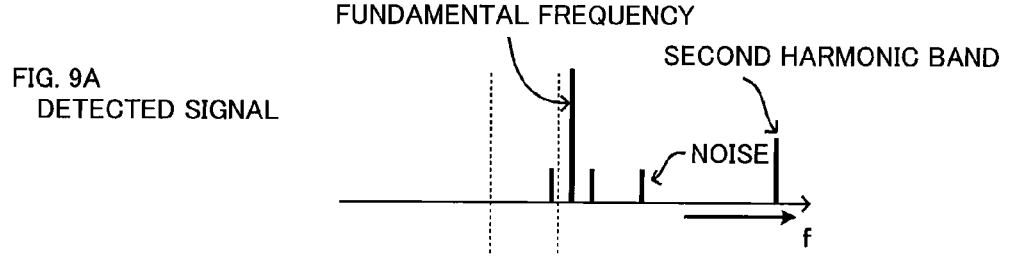
FIG. 9 illustrates operations according to the band pass filter and the second order differential property in a second state (during-exercise state) of heart beat.

FIG. 9A represents the frequency components of a detected signal (heart beat waveform) during exercise, and it is assumed that both the fundamental frequency and the second harmonic exist in the higher frequency domain than the higher band frequency F2. It is to be noted that the fundamental frequency is assumed to be a frequency lower than the high-frequency side frequency F3 of the second-order differential property.

Figure 9B:
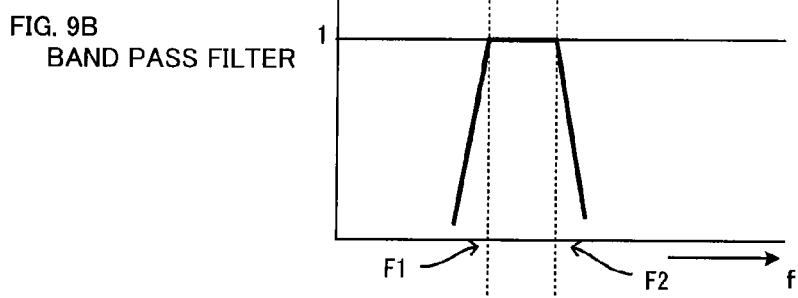
Figure 9C:
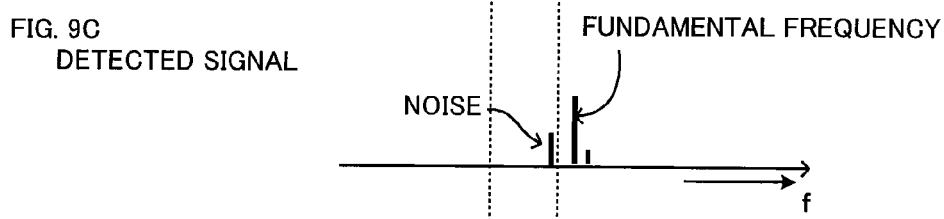

The signal as shown in FIG. 9C represents a frequency components obtained by allowing the aforementioned frequency components as shown in FIG. 9A to pass through the band pass filter as shown in FIG. 9B. The band pass filter removes the noise component and the second harmonic existing in the frequency higher than the higher band frequency F2.

Figure 9D:
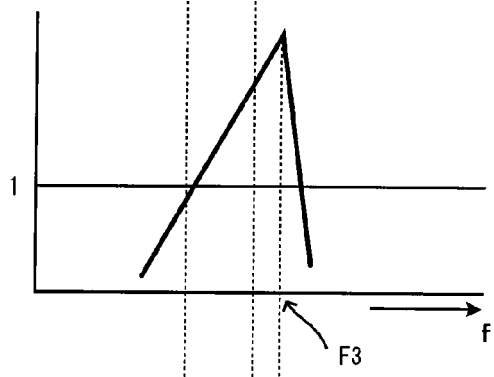
Figure 9E:
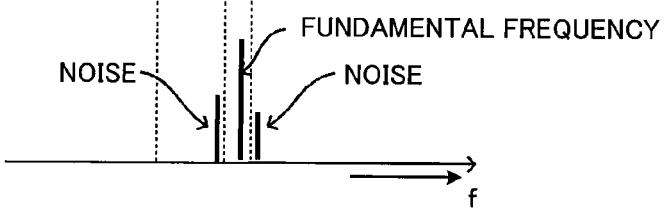

The signal as shown in FIG. 9E represents frequency components that are obtained by subjecting the signal after passing through the band pass filter to the signal amplification according to the second-order differential property as shown in FIG. 9D. According to the second-order differential property, the frequency component around the high-frequency side frequency F3 is amplified more drastically. In FIG. 9D, the frequency component of the fundamental frequency and the noise component are emphasized and amplified.

Hereinafter, with reference to FIG. 10 to FIG. 15, an example of signal processing by the heart beat signal generating processor A (narrowband signal processing) will be described. FIG. 10 and FIG. 11 respectively illustrate the state before processing and the state after processing when no exercise is performed. FIG. 12 and FIG. 13 respectively illustrate the state before processing and the state after processing immediately after the exercise is initiated. FIG. 14 and FIG. 15 respectively illustrate the state before processing and the state after processing during exercise. In each of the figures, the reference mark (a) indicates a waveform, and the reference mark (b) indicates a frequency component.

Firstly, a situation where no exercise is performed will be explained.

Figure 10A:
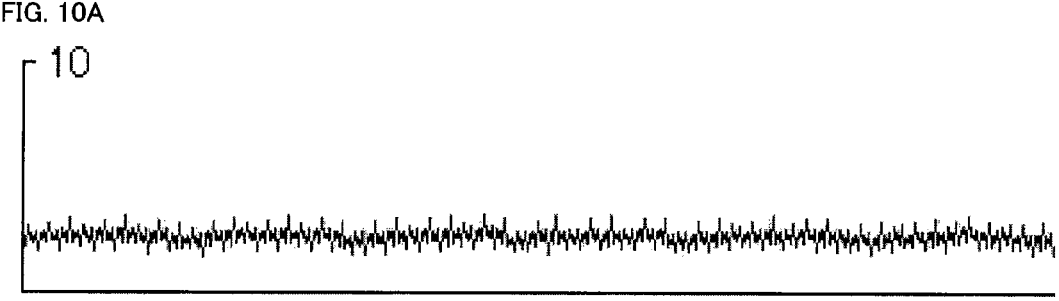
FIG. 10 illustrates the waveform and frequency component before processing in the non-exercise state.
Figure 11A:
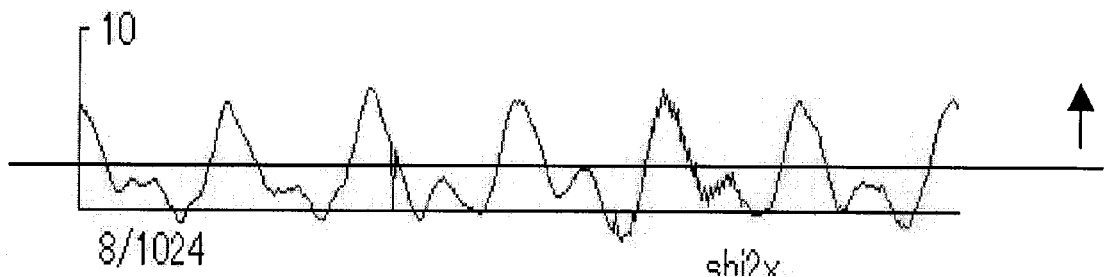
FIG. 11 illustrates the waveform and frequency component after processing in the non-exercise state.

As illustrated in FIG. 10A, the original waveform before the narrowband signal processing during non-exercise shows low amplitude, since the blood stream remains at a low level, and further, the noise level is low because any exercise is performed. FIG. 11A illustrates a waveform that is obtained by subjecting this waveform to the narrowband signal processing. According to the waveform distortion by the narrowband signal processing, the waveform is deformed from the original waveform, but the S/N ratio is enhanced. It is to be noted that the solid line in FIG. 11A represents a curvature component of the higher band frequency F2, and the part of the waveform on and higher than this line indicates the primary component of the heart beat.

Figure 10B:
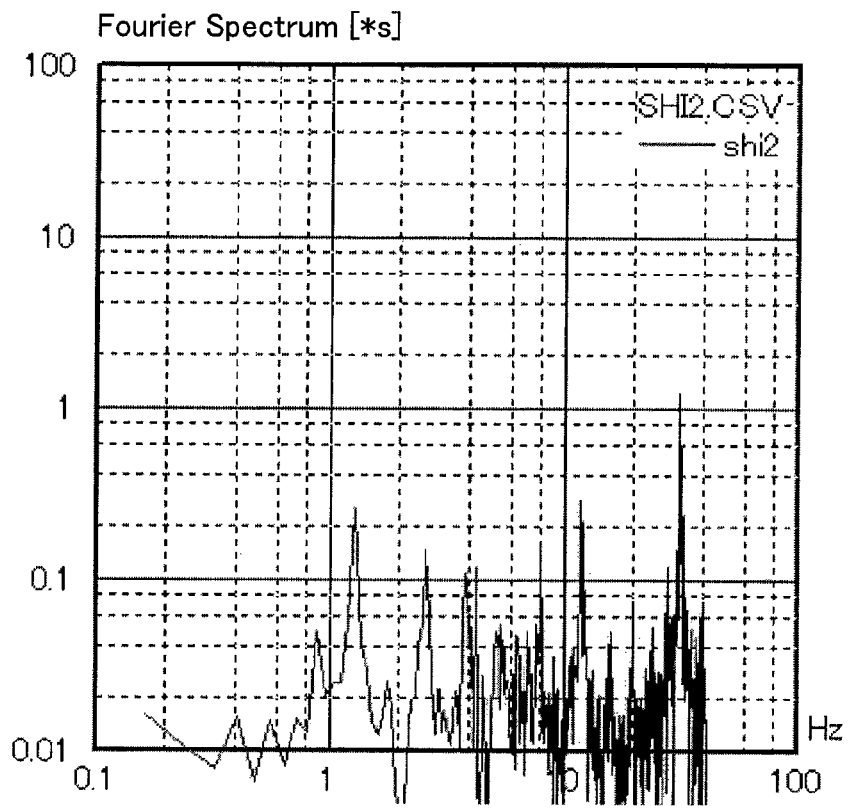
Figure 11B:
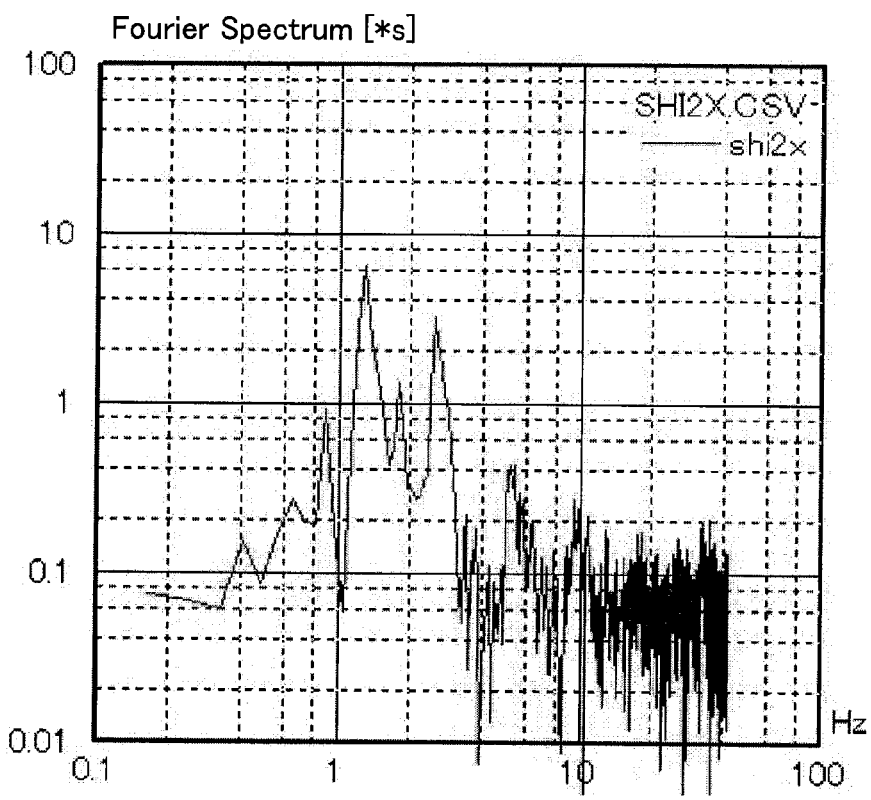

When the frequency components of FIG. 10B and FIG. 11B are compared, the signal level within the frequency ranges F1 to F3 is enhanced according to the narrowband signal processing.

Figure 12A:
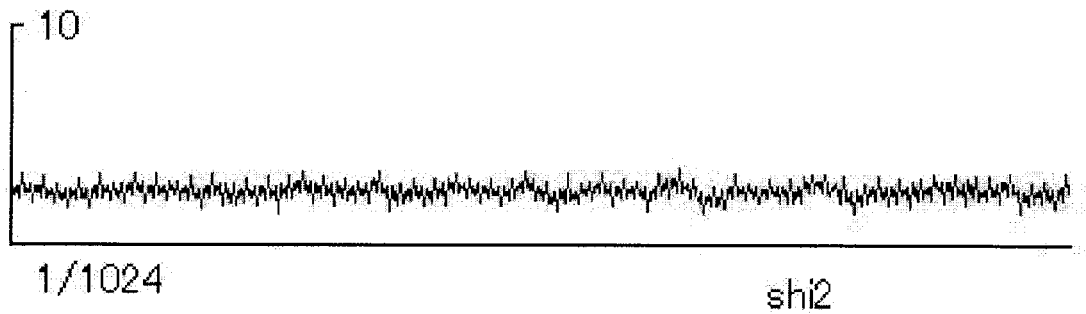
FIG. 12 illustrates the waveform and frequency component before processing just after the exercise initiation.

Next, a situation immediately after the exercise initiation will be explained. As shown in FIG. 12A, in the original waveform before the narrowband signal processing immediately after initiation the exercise, the blood stream is at the low level, and therefore the amplitude of the heart beat waveform is low. However, since the exercise is initiated, the noise level becomes higher, and therefore, the S/N ratio is deteriorated.

Figure 13A:
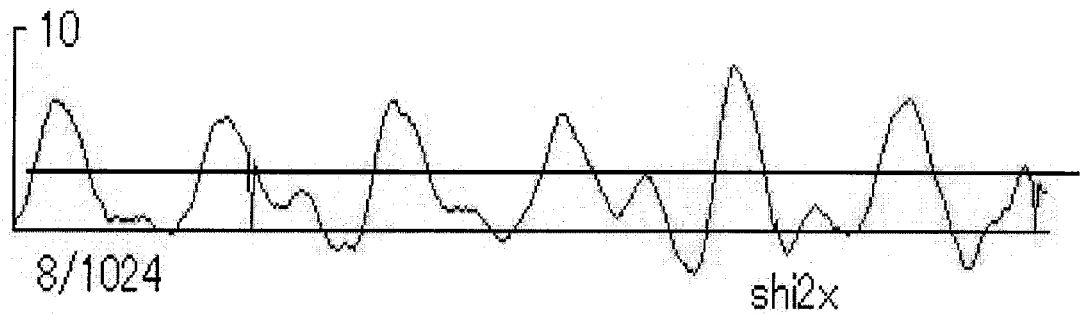
FIG. 13 illustrates the waveform and frequency component after processing just after the exercise initiation.

FIG. 13A illustrates a waveform that is obtained by subjecting this waveform to the narrowband signal processing. This waveform is deformed from the original waveform by the waveform distortion, according to the narrowband signal processing. However, the second harmonic is emphasized and amplified, rather than the noise, and therefore the S/N ratio is enhanced. It is to be noted that the solid line in FIG. 13A represents a curvature component of the higher band frequency F2, and the part of the waveform on and higher than this line indicates the primary component of the heart beat.

Figure 12B:
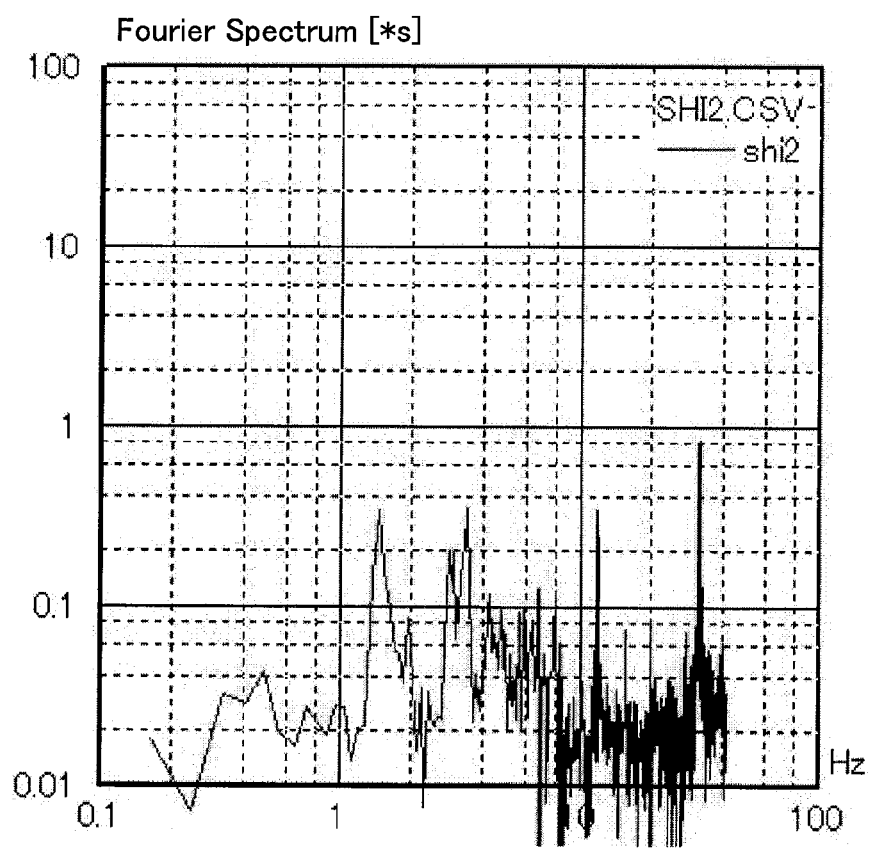
Figure 13B:
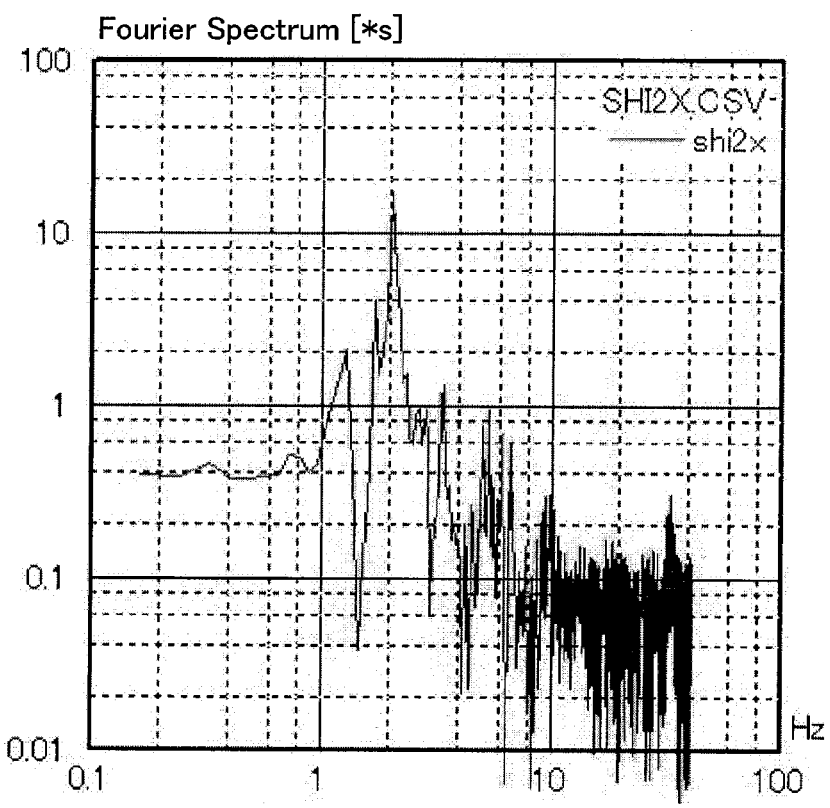

When the frequency component in FIG. 12B is compared with the frequency component in FIG. 13B, the signal level in the frequency range from F1 to F3 is enhanced by the narrowband signal processing.

Next, a situation when the exercise is being performed will be explained.

Figure 14A:
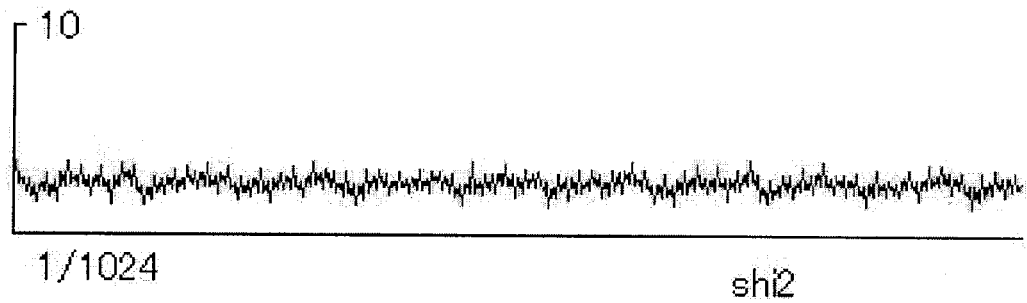
FIG. 14 illustrates the waveform and frequency component before processing during exercise.

As shown in FIG. 14A, in the original waveform before the narrowband signal processing during the exercise, the heart beat and the blood stream are increased, and the amplitude of the heart beat waveform is increased.

Figure 15A:
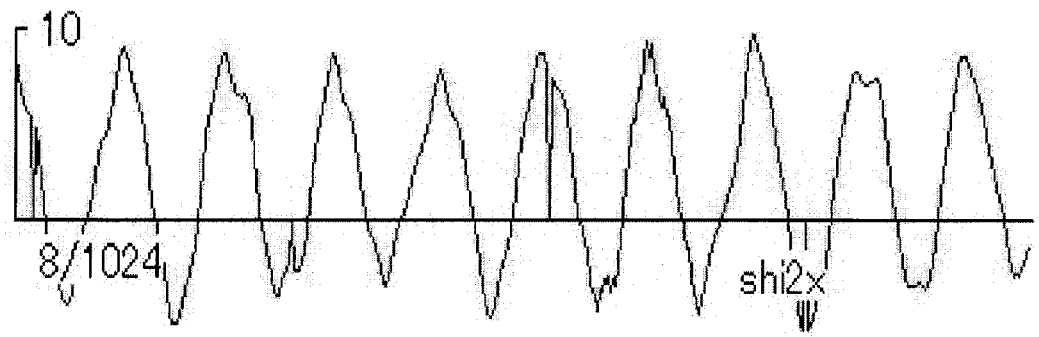
FIG. 15 illustrates the waveform and frequency component after processing during exercise.

FIG. 15A illustrates a waveform that is obtained by subjecting the waveform to the narrowband signal processing. In this waveform, the signals on the high-frequency side are amplified by the narrowband signal processing. In this situation, if there is a noise component on the high-frequency side, a waveform distortion is generated in which the peak point varies due to the amplification of the noise component.

Figure 14B:
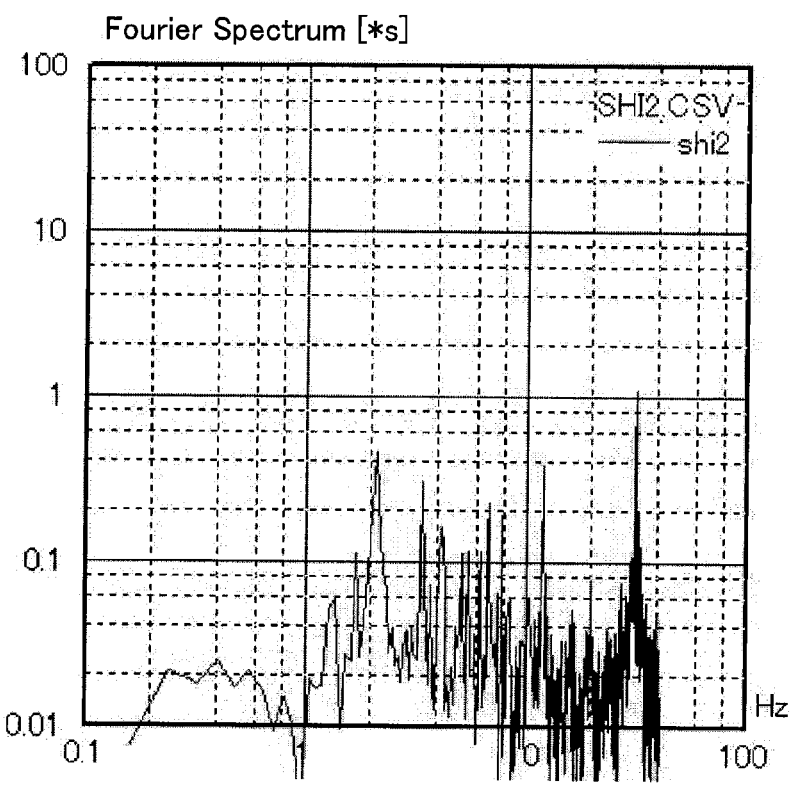
Figure 15B:
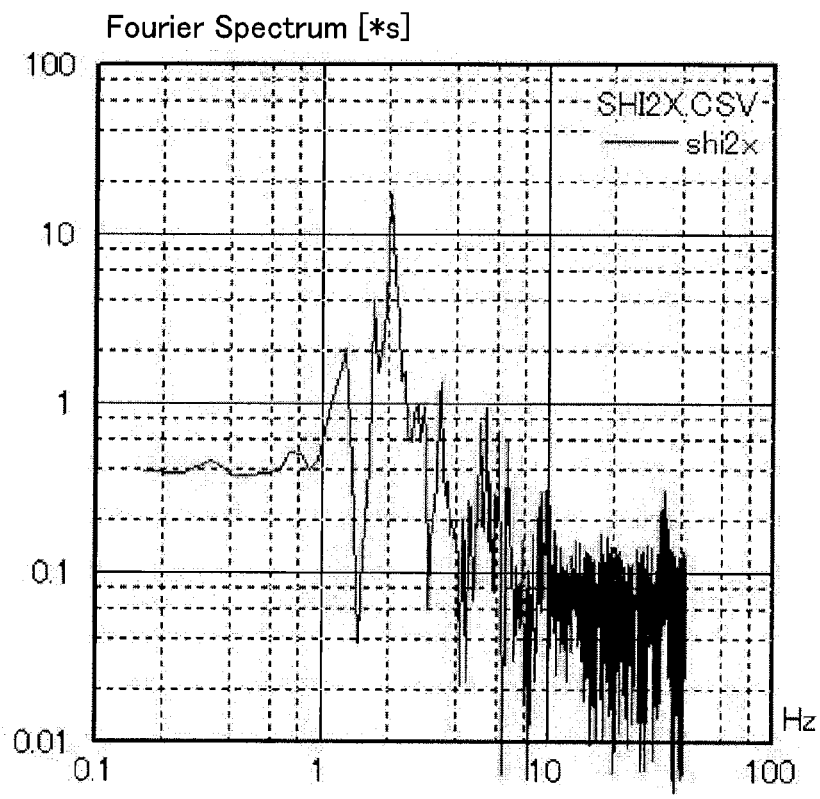

In addition, when the frequency component in FIG. 14B is compared with the frequency component in FIG. 15B, the signal level including the noise in the frequency range from F1 to F3 is enhanced by the narrowband signal processing.

Next, with reference to FIG. 16, one configuration example of the narrowband signal processing will be explained. It is to be noted here that a digital filter constitutes the example as shown in FIG. 16, where an input signal is assumed as a sampling signal.

In general, the digital filter is made up of delay units 50, coefficient multipliers 51, and adders 52.

Figure 16A:
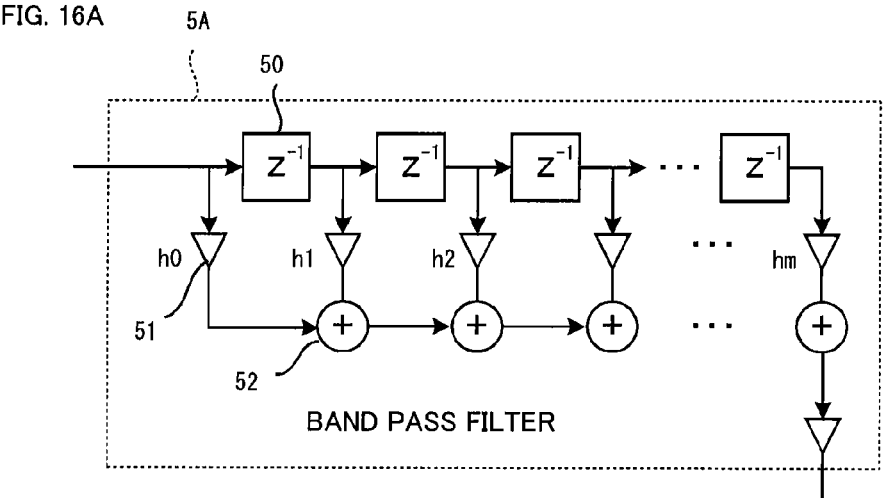
FIG. 16 illustrates one configuration example of the narrowband signal processing.
Figure 16B:
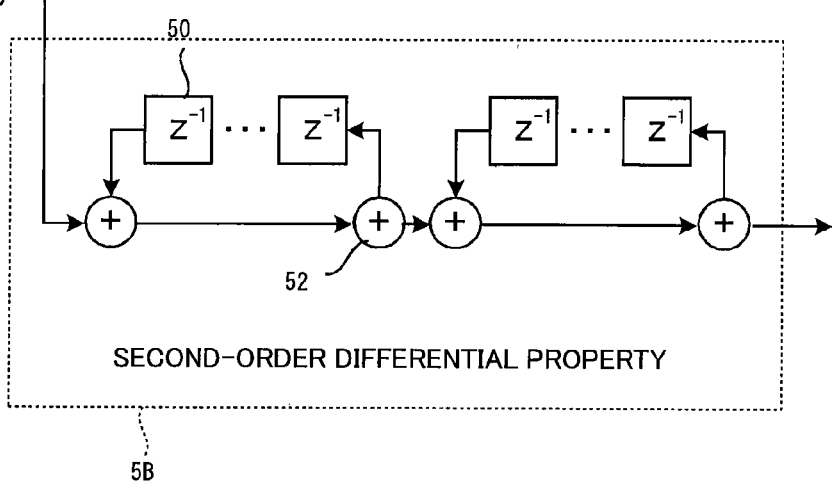

FIG. 16A illustrates a configuration example of the band pass filter that constitutes the narrowband signal processing according to the present invention. FIG. 16B illustrates a configuration example of the second-order differential property that constitutes the narrowband signal processing according to the present invention.

The band pass filter illustrated in FIG. 16A is an example of FIR (Finite Impulse Response) model. The frequency F1 and the frequency F2 in the passband of the narrow band are set by using the sampling period and the factors h0 to hm defined by the coefficient multipliers 51.

The second-order differential property as illustrated in FIG. 16B sets the differential upper limit F3, by the sampling period and the number of units which are set as the delay units for backward difference.

In the example discussed above, there is illustrated a case of the second-order differential property, as the amplification characteristic of the signal amplification. However, the amplification characteristic is not limited to the second-order differential property, but it may be a first-order differentiation or higher-order differential property. In addition, it may be the amplification characteristic other than the differential property.

FIG. 17 illustrates amplification characteristics of the signal amplification according to the present invention. FIG. 17A to FIG. 17C illustrate examples of the amplification characteristics according to the differential property. FIG. 17D is an example of step-like amplification characteristic.

Figure 17A:
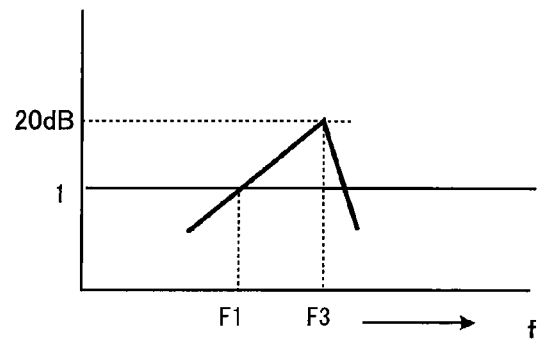
FIG. 17 illustrates amplification characteristics of the signal amplification according to the present invention.
Figure 17B:
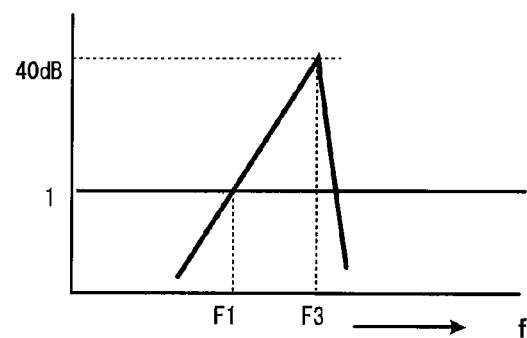
Figure 17C:
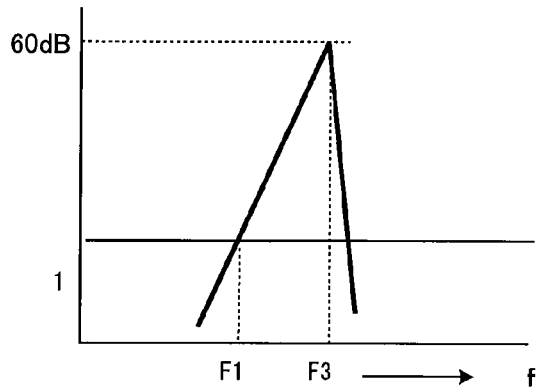

FIG. 17A illustrates a differential property of the first-order differentiation, FIG. 17B illustrates a differential property of the second-order differentiation, and FIG. 17C illustrates a differential property of the third-order differentiation. In each of the differential property, the gain varies depending on the number of order of the differentiation. In the first-order differentiation, the gain is 20 dB, in the second-order differentiation, the gain is 40 dB, and in the third-order differentiation, the gain is 60 dB. It is to be noted here that the numerical value of each dB represents a gain with respect to a predetermined frequency bandwidth.

Any order of the differential property may be employed, however, in here, an example is shown using the second-order differentiation, which can obtain the gain of 40 dB, for instance, considering the level of the S/N ratio of the heart beat signal being detected, the circuit configuration of the signal processing, cost-benefit performance, and the like.

Figure 17D:
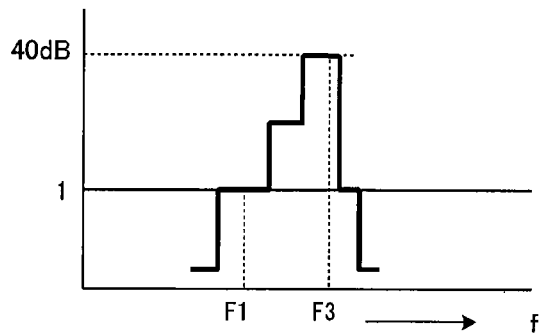

As the amplification characteristic to achieve a higher gain for a higher frequency domain, in addition to the differential property, the step-like gain as shown in FIG. 7(d) may be employed. In FIG. 17D, the gain around the frequency F1 is set to "1", the gain around the high frequency F3 is set to be higher, and therebetween the gain varies stepwise. It is to be noted that the number of steps can be set arbitrarily.

Figure 18:
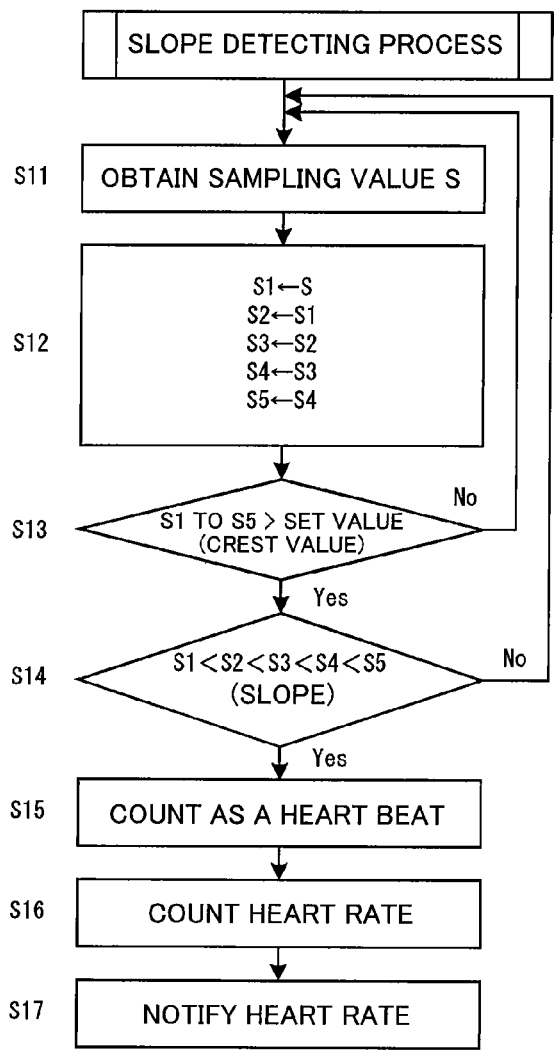
FIG. 18 is a flowchart to explain waveform distortion detection (slope detection) according to the present invention.
Figure 19:
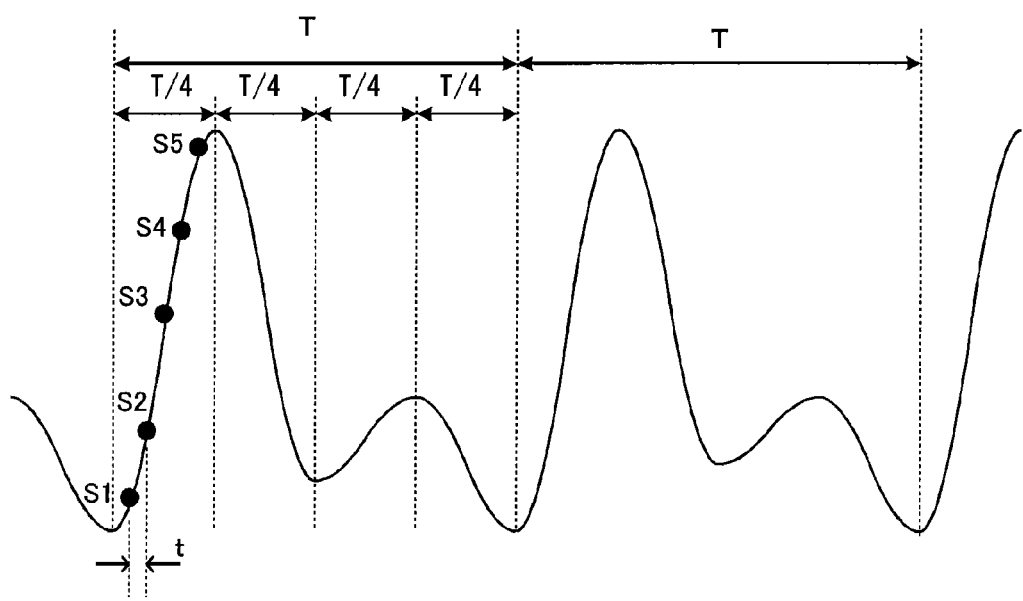
FIG. 19 illustrates a relationship between the period and the slope part.

Next, the waveform distortion detection (slope detection), being the heart beat detecting processor C of the present invention will be explained, with reference to the flowchart of FIG. 18, FIG. 19 illustrating a relationship between the period and the slope part, FIG. 20 illustrating the waveform distortion according to the fundamental frequency, FIG. 21 illustrating the slope detection using the sampling point, and FIG. 22 being an actual example of the waveform distortion detection.

In the flowchart shown in FIG. 18, the waveform distortion detection (slope detection) is performed by using sampling values, which are obtained by sampling the detected waveform at regular intervals (S11).

In FIG. 19, when the period of the heart beat is assumed as T, the waveform distortion detection is performed at the duration of time, i.e., a quarter of the period T of the heart beat waveform. In order to perform the waveform distortion detection within the duration of time T/4, when the sampling period is assumed as t, successive sampling points (S1 to S5) are detected, the number of which corresponds to the value obtained by dividing the duration of time T/4 by the sampling period t ((T/4)/t). If the values of the sampling points (S1 to S5) are larger than the frequency component around the frequency of the second harmonic of the highest heart beat waveform during non-exercise, and the values monotonously increase or monotonously decrease, the waveform distortion is detected as a heart beat.

For example, if the maximum heart beat F3 during exercise is assumed as 3.367 Hz, for instance, the slope detection is performed at the duration of time equal to or less than a quarter of this period (68 msec) Here, when the sampling period is assumed as 12 msec, the detection is performed at the sampling number of times of 5.67 or less. It is to be noted here that if the sampling number of times is larger than this value 5.67, the sampling goes over the quarter period, and therefore disabling the slope detection.

In view of this situation above, five times are set as the sampling number of times. A sampling value obtained at S1 is collected for each of the sampling points, the number of which is required at least for obtaining angle of the slope, and those values are stored in S1 to S5, sequentially. It is to be noted that each sampling value is replaced every time the sampling is performed, and the sampling value having been replaced is discarded sequentially from the oldest one (S12).

As a first condition for detecting the waveform distortion, it is determined whether or not the values of the sampling points (S1 to S5) are larger than a set value. As the set value, the frequency component around the frequency of the second harmonic of the highest heart beat waveform of the heart beat during non-exercise may be employed. As discussed above, if the values are larger than this set value, it is possible to remove noise component (S13).

Next, as the second condition for detecting the waveform distortion, it is determined whether or not the slope of the sampling points (S1 to S5) indicates continuous monotonous increase or monotonous decrease within a predetermined period.

FIG. 20 illustrates the determinations according to the first condition and the second condition. In FIG. 20A, H represents the set value being the first condition.

In the case of FIG. 20A, all the sampling values S1 to S5 are larger than the set value H being the first condition, and the sampling values S1 to S5 have the relationship, S1<S2<S3<S4<S5, and therefore the second condition is satisfied. Then, it is determined as one heart beat according to this slope part.

In the case of FIG. 20B, the sampling values S1 to S5 have the relationship, S1<S2<S3<S4<S5, and the second condition is satisfied. However, the sampling value S1 is equal to or less than the set value H, and therefore it is not determined as one heart beat according to this slope part.

In the case of FIG. 20C, all the sampling values S1 to S5 are larger than the set value H, satisfying the first condition, but the sampling value S5 is smaller than the sampling value S4 and the second condition of S1<S2<S3<S4<S5 is not satisfied. Therefore, it is not determined as one heart beat according to this slope part (S14).

If both of the first and the second conditions in S13 and in S14 are satisfied, it is determined that there has been one heart beat according to this slope part (S15). Then, the heart beat is counted sequentially to obtain a heart rate (S16), and the heart rate being counted is notified. The notification means includes a display, and in addition, it includes data recording on a recording medium and data transmission to other device.

Figure 21A:
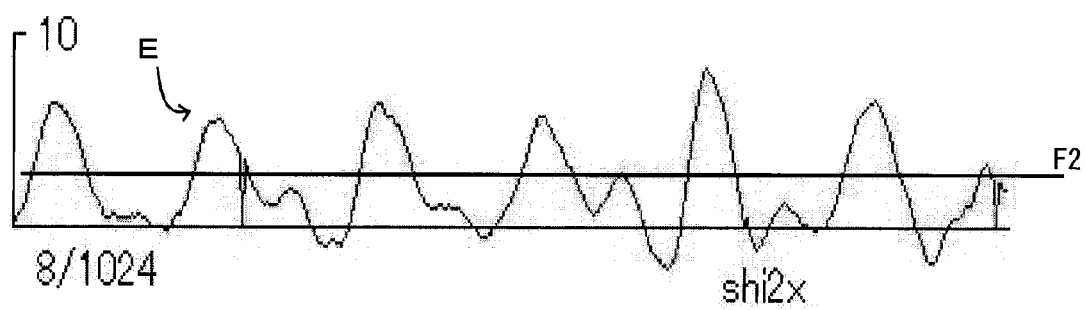
FIG. 21 illustrates the slope detection according to the sampling point.

FIG. 21 illustrates how the second harmonic appears according to the size of the fundamental frequency of the heart beat waveform. FIG. 21A illustrates a case where the fundamental frequency of the heart beat waveform is not higher than the higher band frequency F2 (1.5 Hz). Under this condition, a curvature component (2.68 Hz) E of the F2 (second harmonic) appears. The angle of the slope is determined as to this curvature component E, and the heart beat is determined.

Figure 21B:
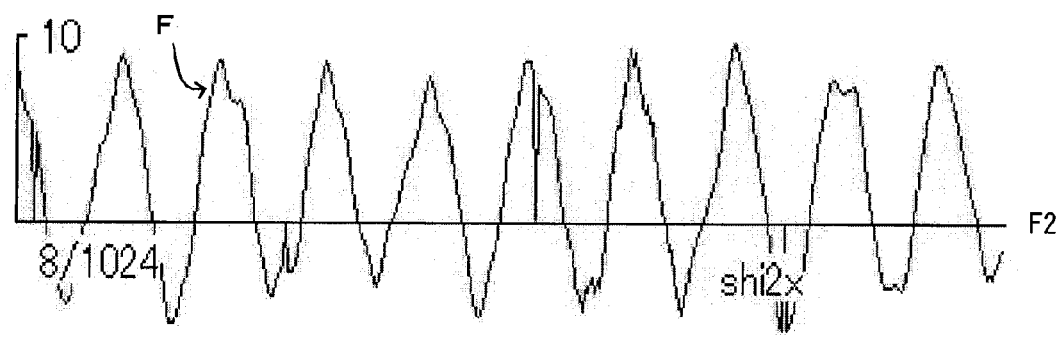

FIG. 21B illustrates a case where the fundamental frequency of the heart beat waveform is between the higher band frequency F2 and the differential upper limit F3 (2.68 Hz). Under this condition, since the higher harmonic is cut off, the curvature component of the F2 (second harmonic) becomes zero, and there appears a curvature component F which is a sine wave itself of the fundamental frequency. The angle of the slope is determined as to this curvature component F, and the heart beat is determined.

Figure 22:
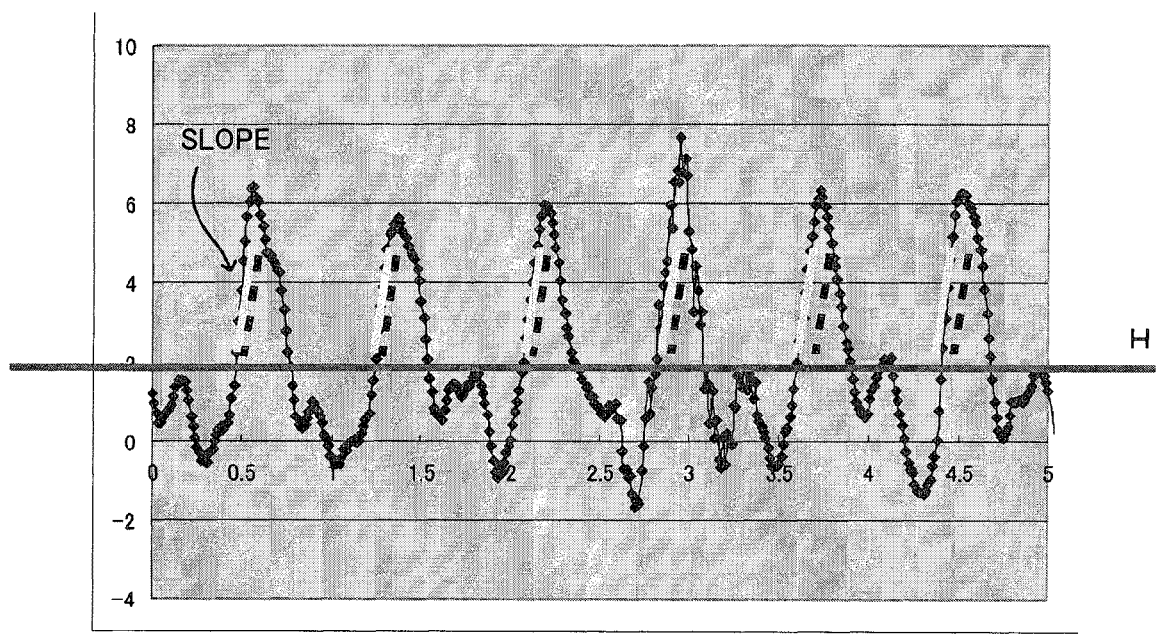
FIG. 22 is an actual example for explaining the waveform distortion detection.

FIG. 22 illustrates an actual example for detecting the waveform distortion. Here, as the fundamental frequency of the heart beat, 3.67 Hz of F3 can be taken. Therefore, in order to detect the slope tending upward, the slope detection is performed in the duration of time not longer than a quarter of the period of the highest heart beat during exercise F3 (68 msec or less). In addition, here, 2 (two) is set as the lowest value of the sampling value (H in FIG. 22).

Figure 23:
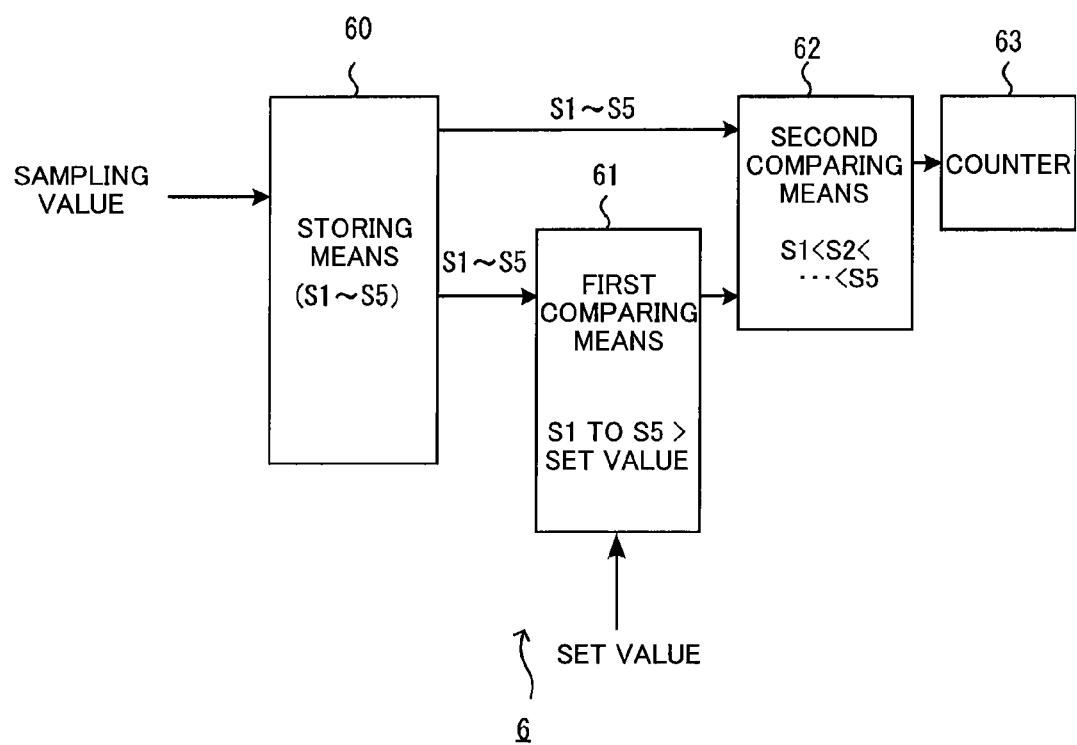
FIG. 23 is a diagram for explaining one configuration example of the waveform distortion detecting unit.
Figure 24:
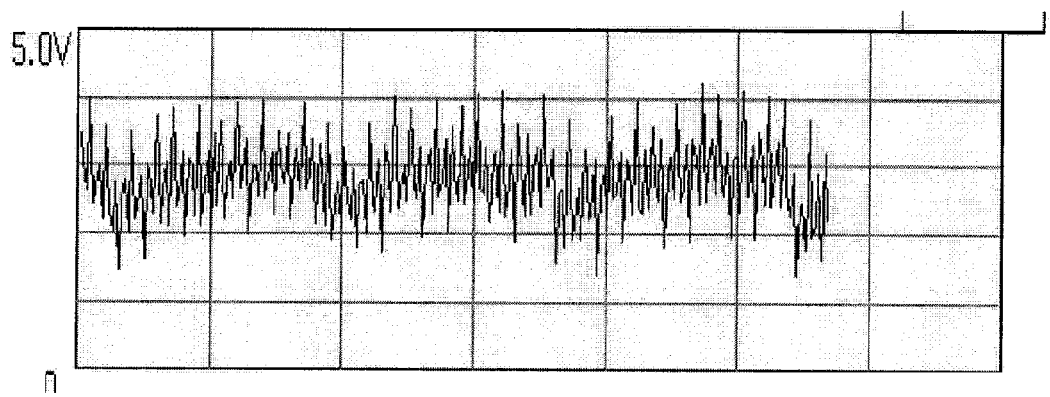
FIG. 24 illustrates one example of the heart beat waveform that is detected by the waveform detecting unit such as the heart beat sensor.
Figure 25A:
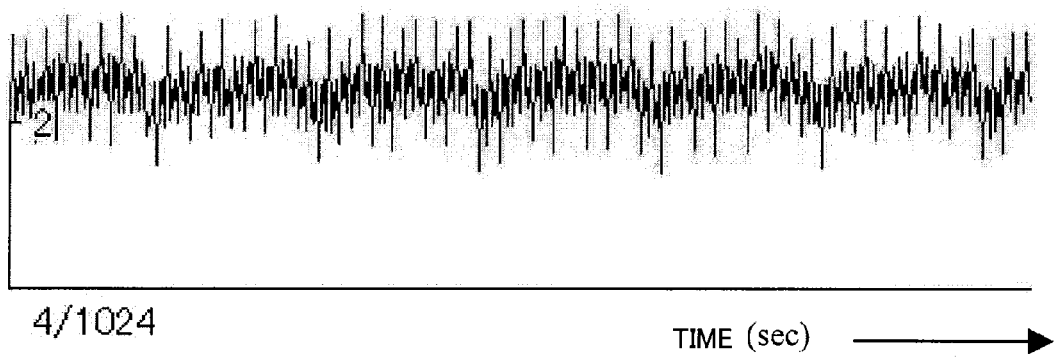
FIG. 25 illustrates an example of each of the noise components included in the heart beat waveform shown in FIG. 24.
Figure 25B:
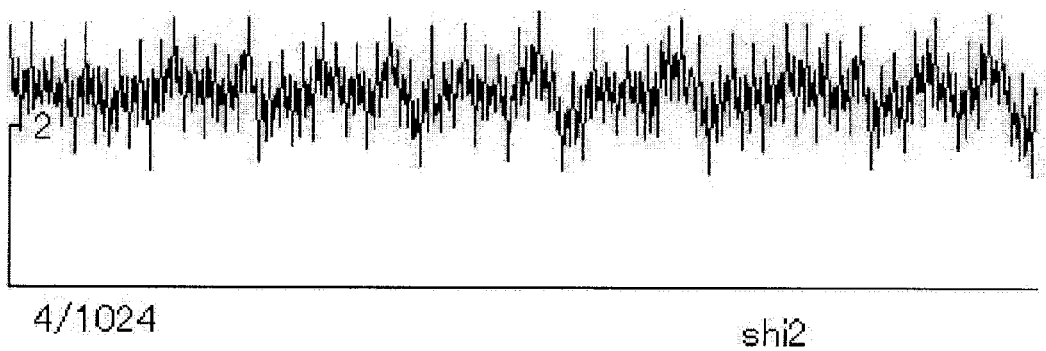
Figure 26A:
FIG. 26 illustrates the frequency characteristic during non-exercise.
Figure 26B:
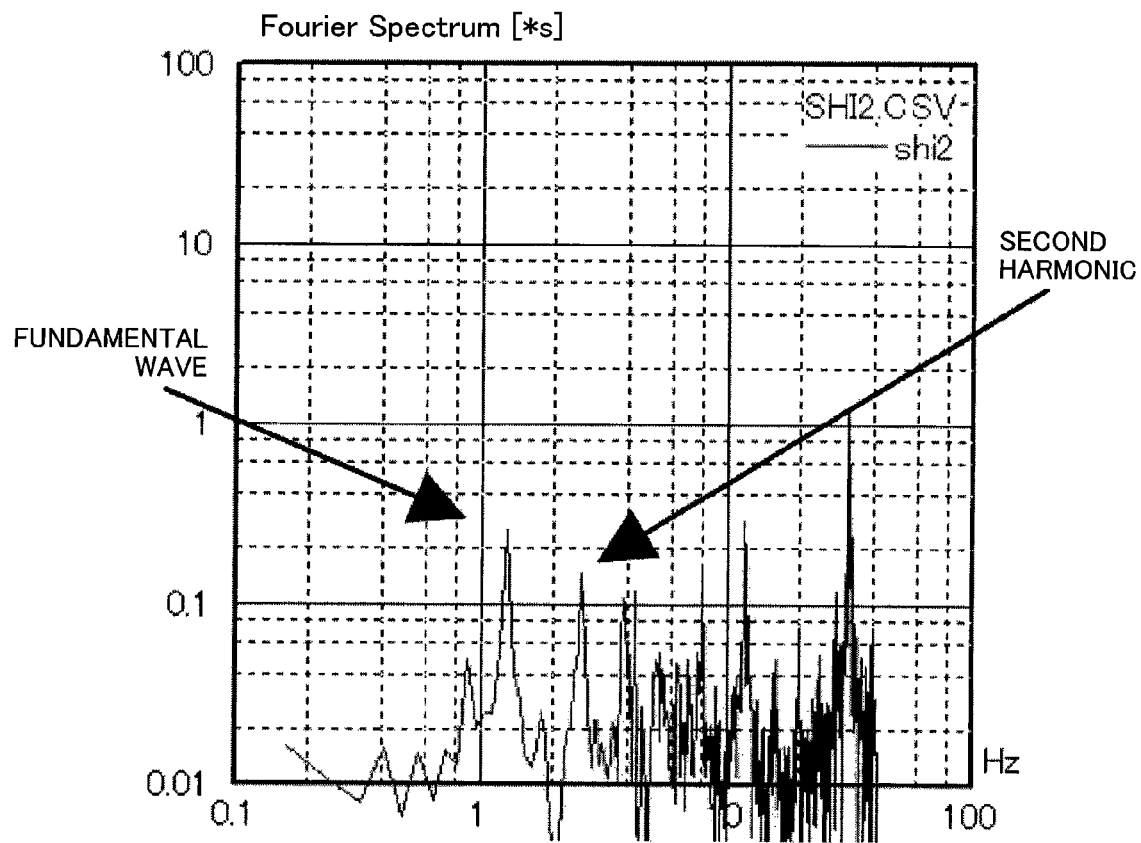
Figure 27A:
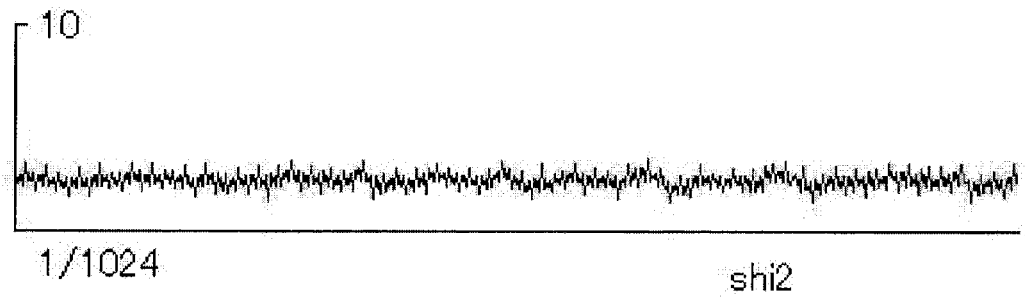
FIG. 27 illustrates the frequency characteristic at the initiation of exercise.
Figure 27B:
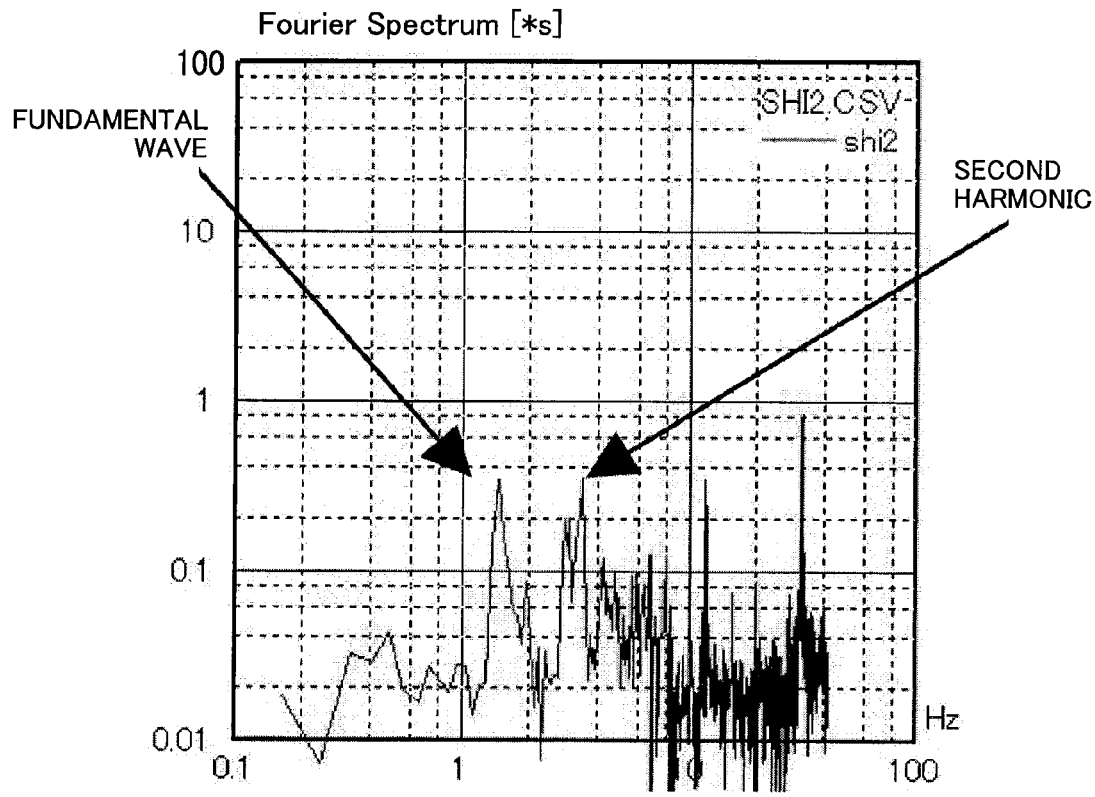
Figure 28A:
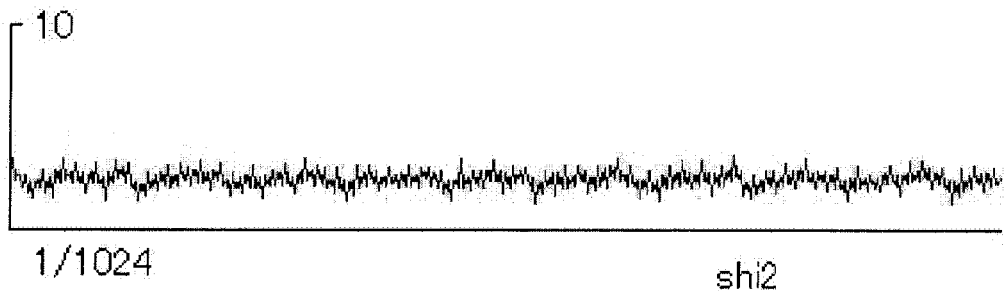
FIG. 28 illustrates the frequency characteristic during exercise.
Figure 28B:
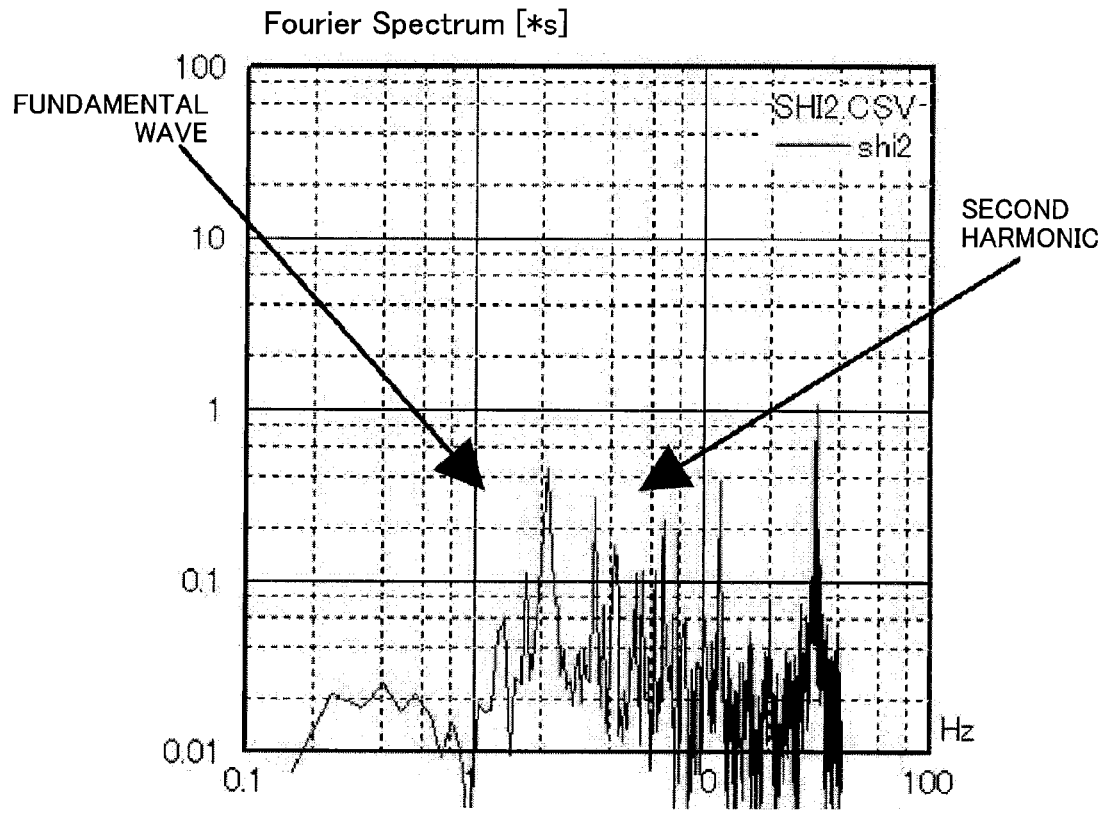
Figure 30A:
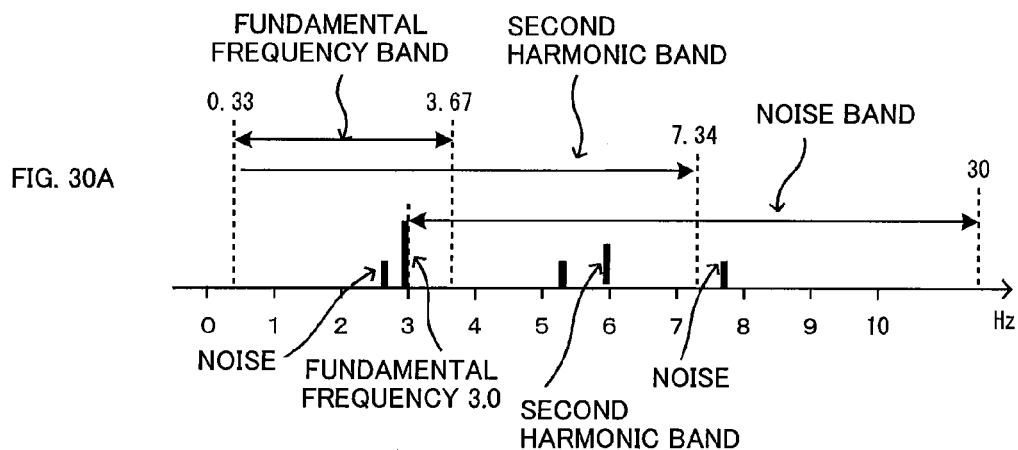
FIG. 30 illustrates an example during exercise (setting the fundamental frequency to 3.0 Hz).
Figure 30B:
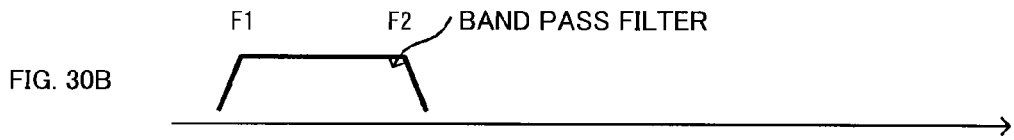
Figure 30C:
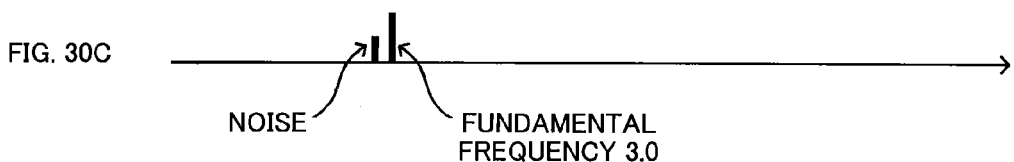

FIG. 23 is a diagram for explaining one configuration example of the waveform distortion detecting unit.

The configuration as shown in FIG. 23 includes a storing means for storing the inputted sampling values S1 to S5, sequentially, a first comparing means 61 for comparing the sampling values S1 to S5 stored in the storing means 60 with the set value, a second comparing means 62 in which a result of the comparison from the first comparing means 61 and the sampling values S1 to S5 stored in the storing means 60 are inputted, and when the sampling values S1 to S5 are larger than the set value, the order of the sizes of the sampling values S1 to S5 is determined, and the counter 63 for counting the heart rate based on the result of the determination from the second comparing means 62.

INDUSTRIAL APPLICABILITY

A method for detecting the heart beat waveform according to the present invention can be applied not only to the heart rate meter, but also to an apparatus that measures a body function using the heart beat as one data, such as a body function measuring apparatus.

What is claimed is:

1. A heart rate meter, comprising:
a heart beat waveform detecting unit for detecting a heart beat waveform of a living body, and
a signal processor for detecting a heart beat from the heart beat waveform, wherein,
the signal processor comprises,
a heart beat signal generating processor for subjecting the heart beat waveform to a signal processing to generate a heart beat signal, and
a heart beat detecting processor for detecting a heart beat from the heart beat signal generated by the heart beat signal generating processor,
wherein, the heart beat signal generating processor comprises a band pass filter that passes a frequency component in a predetermined narrow band to remove a noise component in the frequency band other than the primary component of the heart beat waveform, and
a signal amplifier for amplifying a signal of the frequency component of the heart beat waveform according to a signal amplification characteristic that allows for a gain of the frequency component to increase from around a lower band towards a higher band in the predetermined narrow band such that the gain becomes the highest at the higher band of the predetermined narrow band.

2. The heart rate meter according to claim 1, wherein, the signal amplifier is provided with the amplification characteristic that maximizes an amplification degree around the fundamental frequency of the highest heart beat waveform in a second state of heart beat.

3. The heart rate meter according to claim 2, wherein, the amplification characteristic is provided with a frequency band where the gain is lowered gradually towards a frequency domain higher than the frequency of the highest amplification degree.

4. The heart rate meter according to claim 2, wherein, the second state of heart beat is assumed as during-exercise state.

5. The heart rate meter according to claim 1, wherein, the heart beat detecting processor detects a waveform slope component of the heart beat signal, and when the waveform slope component corresponds to a predetermined waveform slope component, a heart beat is detected.

6. The heart rate meter according to claim 5, wherein, the slope component is a signal variation either during a rise time of the heart beat signal waveform or during a fall time thereof, and alternatively, the signal variations of both during the rise time and the fall time.

7. The heart rate meter according to claim 1, wherein, the heart beat detection processor comprise a waveform distortion detecting unit for detecting a waveform distortion that is added to the heart beat signal, using a crest value and inclination of the heart beat signal as a detecting condition, and for detecting as a heart beat from the waveform distortion, the waveform distortion being detected by the waveform distortion detecting unit.

8. The heart rate meter according to claim 7, wherein, the detecting condition includes that the heart beat signal has a predetermined crest value or higher, and the heart beat signal shows a monotonous increase or a monotonous decrease within a predetermined period, or alternatively, both the monotonous increase and the monotonous decrease are shown.

9. The heart rate meter according to claim 8, wherein, the predetermined crest value is a frequency component around the frequency of the second harmonic of the highest heart beat waveform in the first state of heart beat.

10. The heart rate meter according to claim 9, wherein, the predetermined period is a period range not longer than a quarter of a period of the heart beat waveform.

11. A heart rate meter, comprising:
a heart beat waveform detecting unit for detecting a heart beat waveform of a living body, and
a signal processor for detecting a heart beat from the heart beat waveform, wherein,
the signal processor comprises,
a heart beat signal generating processor for subjecting the heart beat waveform to a signal processing to generate a heart beat signal, and
a heart beat detecting processor for detecting a heart beat from the heart beat signal generated by the heart beat signal generating processor,
wherein, the heart beat signal generating processor comprises a band pass filter that passes a frequency component in a predetermined narrow band to remove a noise component in the frequency band other than the primary component of the heart beat waveform, and
a signal amplifier for amplifying a signal of the frequency component of the heart beat waveform according to a differential property that allows for a gain of the frequency component to increase from around a lower band of the predetermined narrow band towards the direction of a higher band of the predetermined narrow band such that the gain becomes the highest at a predetermined high frequency higher than the frequency component of the higher band of the predetermined narrow band.

12. The heart rate meter according to claim 11, wherein, the filter of the heart beat signal generating processor comprises the band pass filter for allowing passage of the frequency component within the predetermined narrow band, out of the frequency component of the heart beat waveform, so as to remove either of a disturbance noise component and a motion artifact component, or both the disturbance noise component and the motion artifact component, and
the signal amplifier subjects the frequency component that passed through the band pass filter to the signal amplification.

13. The heart rate meter according to claim 12, wherein, the band pass filter is provided with a frequency range as the following; a frequency not lower than a frequency of a second harmonic of a highest heart beat waveform in a first state of heart beat is assumed as a cutoff frequency in a higher band.

14. The heart rate meter according to claim 12, wherein, the band pass filter is provided with a frequency range as the following; a frequency not higher than a frequency of a fundamental frequency of a lowest heart beat waveform in the first state of heart beat is assumed as a cutoff frequency in a lower band.

15. The heart rate meter according to claim 13, wherein, the first state of heart beat is assumed as non-exercise state.

16. The heart rate meter according to claim 11, wherein, the signal amplifier subjects the frequency component of the heart beat waveform to the signal amplification, setting a second-order differential property as the differential property.

17. The heart rate meter according to claim 11, wherein, the signal amplifier subjects the frequency component of the heart beat waveform to the signal amplification, setting the second or higher order differential property as the differential property.

* * * * *